United States Patent [19]

Kato et al.

[11] Patent Number: 5,760,136

[45] Date of Patent: Jun. 2, 1998

[54] SILICON-CONTAINING BLOCK COPOLYMER

[75] Inventors: Kazuhiro Kato; Kazushige Muto, both of Kawagoe; Masahiro Sogo, Osaka, all of Japan

[73] Assignee: Wako Pure Chemical Industries, Ltd., Tokyo, Japan

[21] Appl. No.: 764,780

[22] Filed: Dec. 12, 1996

[30] Foreign Application Priority Data

Dec. 14, 1995 [JP] Japan ............................ 7-347591
Dec. 27, 1995 [JP] Japan ............................ 7-352009

[51] Int. Cl.⁶ .................................................. C08F 8/00
[52] U.S. Cl. ........................ 525/100; 525/479; 528/26; 528/38; 528/22; 526/279
[58] Field of Search .......................... 526/279; 525/100, 525/479; 528/26, 38, 22

[56] References Cited

FOREIGN PATENT DOCUMENTS

| | | |
|---|---|---|
| 0 408 311 | 1/1991 | European Pat. Off. . |
| 56-4533 | 1/1981 | Japan . |
| 59-75911 | 4/1984 | Japan . |
| 63-6045 | 1/1988 | Japan . |
| 63-94503 | 4/1988 | Japan . |
| 1-236211 | 9/1989 | Japan . |
| 2-25411 | 1/1990 | Japan . |
| 4-39315 | 2/1992 | Japan . |
| 4-95017 | 3/1992 | Japan . |
| 4-359912 | 12/1992 | Japan . |
| 4-372675 | 12/1992 | Japan . |
| 5-924 | 1/1993 | Japan . |
| 6-93100 | 4/1994 | Japan . |
| 6-271427 | 9/1994 | Japan . |
| 6-322089 | 11/1994 | Japan . |
| 7-2964 | 1/1995 | Japan . |
| 7-41582 | 2/1995 | Japan . |
| 7-102210 | 4/1995 | Japan . |
| 7-179795 | 7/1995 | Japan . |
| 7-316020 | 12/1995 | Japan . |
| 8-253539 | 10/1996 | Japan . |

*Primary Examiner*—Melvyn I. Marquis
*Attorney, Agent, or Firm*—Armstrong, Westerman, Hattori, McLeland & Naughton

[57] ABSTRACT

A block copolymer comprising siloxane segments, amphoteric monomer units and/or cationic nonomer units, and if necessary monomer units of precursors thereof, and nonionic monomer units, obtained by polymerization in the presence of a special azo group-containing polysiloxane compound is useful as paint resins, coating resins and base materials for hair cosmetics.

28 Claims, No Drawings

SILICON-CONTAINING BLOCK COPOLYMER

BACKGROUND OF THE INVENTION

The present invention relates to a novel block copolymer which is very useful as, for example, a paint resin, a coating resin or a base material for hair cosmetic.

Silicone compounds are characterized by their excellent water repellency and low coefficient of friction. As processes utilizing such a characteristic of the silicone compounds, JP-A 63-94503 and JP-A 63-6045, for example, disclose a process comprising adding a polysiloxane to a vinyl chloride resin, and a process comprising spraying a silicone on a vinyl chloride resin to impart water repellency to the resin. The process of adding a polysiloxane to a vinyl chloride resin, however, is disadvantageous in that the vinyl chloride resin and the polysiloxane which are not compatible with each other should be mixed, so that the polysiloxane appears at the resin surface, resulting in low weather resistance and chemical resistance. The process of spraying a silicone on a vinyl chloride resin is disadvantageous in that the resin surface is sticky and that the weather resistance and the chemical resistance are deteriorated.

On the other hand, JP-A 7-102210 discloses a process comprising coating a vinyl chloride resin with a vinyl chloride-based block polymer, and JP-A 7-41582 discloses a process comprising coating a vinyl chloride resin with a ternary copolymer of a polyorganosilsesquioxane macromonomer, a polydialkylsiloxane macromonomer and a vinyl monomer, followed by three-dimensional curing.

The process disclosed in JP-A 7-102210 is a treating process comprising coating a vinyl chloride-based block polymer on a similar resin, a vinyl chloride resin. The vinyl chloride-based block polymer is compatible with the similar resin, the vinyl chloride resin, but when there is used a resin not similar to and not compatible with the vinyl chloride-based block polymer, there are the following problems: the block polymer does not adhere to the substrate resin if the interaction between them is not sufficient; and the weather resistance and the chemical resistance are not sufficient. The process disclosed in JP-A 7-41582 is disadvantageous, for example, in that a reaction for forming a three-dimensional structure is necessary after the coating, and that since the reactive polyorganosilsesquioxane macromonomer is used, extreme care should be taken to prevent three-dimensional curing in the synthesis of a resin for surface treatment.

JP-A 4-372675 discloses a process comprising adding a polymerizable unsaturated carboxylic acid in the synthesis of a vinyl-silicone based block polymer to introduce units having a carboxyl group into the block polymer, and thereby improving the adhesive properties. The introduction of the carboxyl groups improves the adhesive properties, but it tends to have an undesirable influence on a substrate to be coated with the block polymer because the resin itself becomes acidic. When the resin is neutralized with a base such as sodium hydroxide in order to avoid the undesirable influence, the resin becomes basic because the carboxylic acid is weakly acidic, or the ester group or amide group in a macroazoinitiator tends to be hydrolyzed by the base, resulting in a low weather resistance.

As base materials for hair cosmetics, there are known, for example, nonionic base materials and cationic base materials, which are obtained by use of, for instance, polymers or copolymers of N-vinylpyrrolidone (JP-B 56-4533, JP-A 59-75911, etc.) and anionic base materials obtained by use of, for instance, silicone type copolymers (JP-A 4-359912, JP-A 2-25411, JP-A 5-924, etc.).

The nonionic base materials and the cationic base materials, however, are generally disadvantageous in being poor in moisture resistance. The anionic base materials are superior to the nonionic base materials in moisture resistance but are disadvantageous, for example, in that the hair treated by the materials is not natural. Therefore, in order to solve these problems, a mixture of various base materials is used, but no satisfactory base material for hair cosmetic has been obtained.

SUMMARY OF THE INVENTION

The present invention was made in view of such conditions and is intended to provide a novel block copolymer. When used in a paint composition or the like, the block copolymer can provide the composition as one which is excellent in weather resistance, water repellency, adhesive properties, etc. When used in a base material for hair cosmetic, the block copolymer can provide the base material as one which is excellent in moisture resistance, setting ability and elasticity, permits smooth combing and gives flexibility to hair.

The present invention provides a block copolymer comprising, as constituent units, (a) siloxane segments, (b) amphoteric monomer units and/or cationic monomer units, and if necessary (c) monomer units of precursors of amphoteric or cationic monomer, and/or (d) nonionic monomer units.

The present invention also provides a process for producing a block copolymer which comprises polymerizing an amphoteric monomer and/or a cationic monomer, and optionally a nonionic monomer, in the presence of an azo group-containing polysiloxane compound.

The present invention further provides a process for producing a block copolymer which comprises polymerizing an amphoteric monomer and/or a cationic monomer, their precursor monomer, and optionally a nonionic monomer, in the presence of an azo group-containing polysiloxane compound.

The present invention still further provides a process for producing a block copolymer which comprises polymerizing a precursor monomer of an amphoteric or cationic monomer, and optionally a nonionic monomer, in the presence of an azo group- containing polysiloxane compound, and then making the precursor monomer units of the resulting block copolymer amphoteric and/or converting them to a quaternary salt.

The present invention still further provides a process for producing a block copolymer which comprises polymerizing an amphoteric monomer and/or a cationic monomer, their precursor monomer, and optionally a nonionic monomer, in the presence of an azo group-containing polysiloxane compound, and then converting the precursor monomer units of the resulting block copolymer to a quaternary salt and/or making them amphoteric.

DESCRIPTION OF THE PREFERRED EMBODIMENTS

The block copolymer of the present invention includes, for example, those described in (1) to (3) below. (1) Block copolymers comprising (a) polysiloxane segments having repeating units of, for example, the formula [1a]:

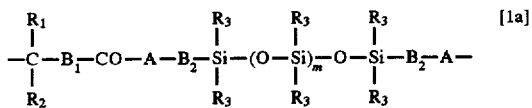

wherein $R_1$ is a hydrogen atom or a lower alkyl group; $R_2$ is a lower alkyl group or a cyano group; A is NH or O; $B_1$ is an alkylene group which may have one or more oxygen atoms; $R_3$ is a hydrogen atom, an alkyl group, a haloalkyl group or an aryl group; $B_2$ is a lower alkylene group which may have one or more oxygen atoms and/or an aromatic ring; and m is zero or an integer of 1 to 200, or polysiloxane segments consisting of a combination of repeating units of the above formula [1a] and repeating units of, for example, the formula [2]:

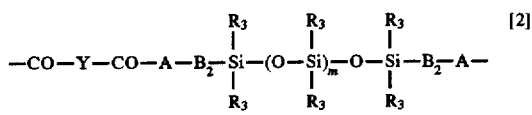

wherein —CO—Y—CO— is a dibasic acid residue; and $R_3$, A, $B_2$ and m are as defined above, (b) amphoteric monomer units of, for example, the formula [3a]:

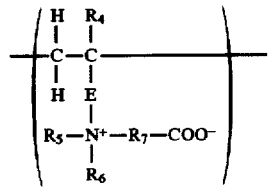

wherein $R_4$ is a hydrogen atom or a lower alkyl group; E is a direct link or —$COOR_8$— (wherein $R_8$ is a lower alkylene group); $R_5$ and $R_6$ are independently a lower alkyl group or an aryl group, $R_5$ and $R_6$ being able to form a ring together with the nitrogen atom, and said ring being able to contain NH or O; and $R_7$ is a divalent hydrocarbon group, and/or cationic monomer units of the formula [4a]:

wherein $R_4$ is a hydrogen atom or a lower alkyl group; E is a direct link or —$COOR_8$— (wherein $R_8$ is a lower alkylene group); $Z^+$ is a trialkylammonium ion or a cyclic ammonium ion; and $W^-$ is an anion.

(2) Block copolymers comprising (a) polysiloxane segments having repeating units of, for example, the above formula [1a] or polysiloxane segments consisting of a combination of repeating units of the above formula [1a] and repeating units of, for example, the above formula [2], (b) amphoteric monomer units of, for example, the above formula [3a] and/or cationic monomer units of the above formula [4a], and (c) units of a precursor monomer of an amphoteric or cationic monomer (hereinafter abbreviated as "precursor monomer units") which are represented by, for example, the formula [5a]:

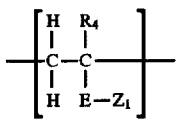

wherein $Z_1$ is a dialkylamino group or a cyclic amino group; and $R_4$ and E are as defined above.

(3) Block copolymers obtained by introducing, into the block copolymer described in (1) or (2) above, nonionic monomer units of, for example, the formula [6a]:

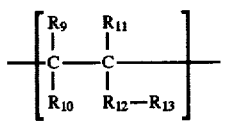

wherein $R_9$ is a hydrogen atom, a lower alkyl group or a halogen atom; $R_{10}$ is hydrogen atom, a lower alkyl group, a halogen atom, an alkyloxycarbonyl group or a formyl group; $R_{11}$ is hydrogen atom, a lower alkyl group, a halogen atom or an alkyloxycarbonyl group; $R_{12}$ is an alkylene group which may have one or more double bonds, or a direct link; and $R_{13}$ is a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, a cyano group, an acyloxy group, a formyl group or a hydroxyl group.

The azo group-containing polysiloxane compound used in the present invention includes, for example, those comprising repeating units of, for instance, the formula [1]:

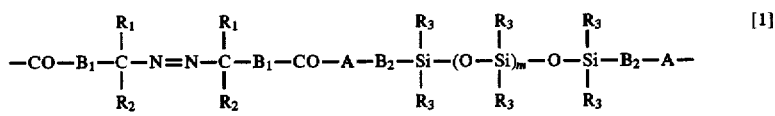

wherein $R_1$, $R_2$, A, $B_1$, $R_3$, $B_2$ and m are as defined above, or a combination of repeating units of the above formula [1] and repeating units of the formula [2]:

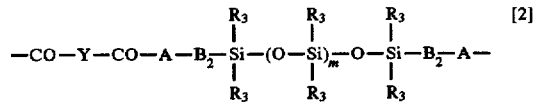

wherein —CO—Y—CO—, $R_3$, A, $B_2$ and m are as defined above.

The amphoteric monomer used in the present invention includes, for example, compounds of the formula [3]:

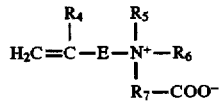

wherein $R_4$, E, $R_5$, $R_6$ and $R_7$ are as defined above.

The cationic monomer used in the present invention includes, for example, compounds of the formula [4]:

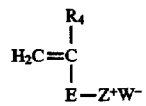

wherein $R_4$, E, $Z^+$ and $W^-$ are as defined above.

The precursor monomer of the amphoteric or cationic monomer (hereinafter abbreviated as "precursor monomer" in some cases) include, for example, compounds of the formula [5]:

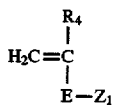

[5]

wherein $Z_1$, $R_4$ and E are as defined above.

This precursor monomer serves both as a precursor monomer of the amphoteric monomer and as a precursor monomer of the cationic monomer.

The nonionic monomer used in the present invention includes, for example, compounds of the formula [6]:

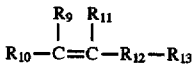

[6]

wherein $R_9$, $R_{10}$, $R_{11}$, $R_{12}$ and $R_{13}$ are as defined above.

In the formulas [1] and [1a], the lower alkyl group represented by each of $R_1$ and $R_2$ may be linear or branched and includes, for example, alkyl groups of 1 to 6 carbon atoms. Specific examples of the lower alkyl group are groups such as methyl, ethyl, n-propyl, isopropyl, n-butyl, isobutyl, tert-butyl, sec-butyl, pentyl, isopentyl, neopentyl, tert-pentyl, 3,3-dimethyl-butyl, 1,1-dimethylbutyl, 1-methylpentyl, n-hexyl, iso-hexyl, etc. In the formula [1], [1a] and [2], the alkyl group represented by $R_3$ may be linear, branched or cyclic and includes, for example, alkyl groups of 1 to 20 carbon atoms. Specific examples of the alkyl group are groups such as methyl, ethyl, n-propyl, isopropyl, n-butyl, isobutyl, tert-butyl, sec-butyl, pentyl, iso-pentyl, neopentyl, tert-pentyl, 3,3-dimethylbutyl, 1,1-dimethylbutyl, 1-methylpentyl, n-hexyl, isohexyl, heptyl, octyl, 2-ethylhexyl, nonyl, decyl, undecyl, dodecyl, hexadecyl, octadecyl, cyclopropyl, cyclopentyl, cyclohexyl, etc. The haloalkyl group represented by $R_3$ includes, for example, haloalkyl groups of 1 to 20 carbon atoms formed by halogenation (e.g. fluorination, chlorination, bromination or iodination) of the above-exemplified alkyl groups. Specific examples of the haloalkyl group are groups such as chloromethyl, bromomethyl, trifluoromethyl, 2-chloroethyl, 3-chloropropyl, 3-bromopropyl, 3,3,3-trifluoropropyl, 2-perfluorooctylethyl, perfluorooctyl, 1-chlorodecyl, 1-chlorooctadecyl, etc. The aryl group represented by R3 includes, for example, groups such as phenyl, tolyl, xylyl, naphthyl, anthryl, etc. In the formulas [1], [1a] and [2], the lower alkylene group represented by $B_1$, i.e., the lower alkylene group which may have one or more oxygen atoms may be linear or branched and includes, for example, alkylene groups of 1 to 6 carbon atoms. When the lower alkylene group has one or more oxygen atoms, it includes lower alkylene groups of 1 to 6 carbon atoms having one or more, preferably 1 to 5, more preferably 1 to 3 oxygen atoms (—O—) at arbitrary positions at the ends or in the chain. Specific examples of the lower alkylene group are groups such as methylene, ethylene, propylene, butylene, 2-methylpropylene, pentylene, 2,2-dimethylpropylene, 2-ethylpropylene, hexylene, —O—CH$_2$—, —O—CH$_2$CH$_2$—, —CH$_2$—O—CH$_2$—, —CH$_2$CH$_2$—O—CH$_2$—, —CH$_2$CH$_2$—O—CH$_2$CH$_2$—, —CH$_2$CH$_2$—O—CH$_2$CH$_2$—O—CH$_2$CH$_2$—, etc. The lower alkylene group is not limited to these groups. In the formulas [1], [1a] and [2], the alkylene group represented by $B_2$, i.e., the alkylene group which may have one or more oxygen atoms and/or an aromatic ring may be linear, branched or cyclic and includes alkylene groups of 1 to 10 carbon atoms. When the alkylene group has one or more oxygen atoms, it includes alkylene groups of 1 to 10 carbon atoms having one or more, preferably 1 to 5, more preferably 1 to 3 oxygen atoms (—O—) at arbitrary positions at the ends or in the chain. When the alkylene group has an aromatic ring, it includes alkylene groups of 1 to 10 carbon atoms having an aromatic ring such as a phenylene group, diphenylene group or the like at arbitrary positions at the ends or in the chain. Specific examples of the alkylene group are groups such as methylene, ethylene, propylene, butylene, 2-methylpropylene, pentylene, 2,2-dimethylpropylene, 2-ethylpropylene, hexylene, heptylene, octylene, 2-ethylhexylene, nonylene, decylene, cyclopropylene, cyclopentylene, cyclohexylene, —CH$_2$—C$_6$H$_4$—, o-xylene-α,α'-diyl, —O—CH$_2$—, —O—CH$_2$CH$_2$—, —CH$_2$—O—CH$_2$—, —CH$_2$CH$_2$—O—CH$_2$—, —CH$_2$CH$_2$—O—CH$_2$CH$_2$—, —CH$_2$CH$_2$—O—CH$_2$CH$_2$—O—CH$_2$CH$_2$—, —CH$_2$—O—C$_6$H$_4$—, etc. The alkylene group is not limited to these groups. In the formula [2], the dibasic acid residue represented by —CO—Y—CO— may be saturated or unsaturated and includes, for example, acid residues of malonic acid, succinic acid, glutaric acid, adipic acid, sebacic acid, phthalic acid, isophthalic acid, terephthalic acid, pimelic acid, suberic acid, azelaic acid, fumaric acid, maleic acid, itaconic acid, malic acid, citraconic acid, mesaconic acid, 1,4-naphthalenedicarboxylic acid, 4,4'-biphenyldicarboxylic acid, etc.

When an azo group-containing polysiloxane compound comprising a combination of repeating units of the formula [1] and repeating units of the formula [2] is used, the proportions of the repeating units of the formula [1] and the repeating units of the formula [2] are not particularly limited so long as the radical-polymerization activity of the azo group-containing polysiloxane compound is not lost. The proportion of the repeating units of the formula [1] is properly chosen in the range of 70 to 50% by weight, and that of the repeating units of the formula [2] in the range of 30 to 50% by weight.

In the formulas [3], [3a], [4], [4a], [5]) and [5a], the lower alkyl group represented by $R_4$ may be linear or branched and includes, for example, alkyl groups of 1 to 6 carbon atoms. Specific examples of the lower alkyl group are groups such as methyl, ethyl, n-propyl, isopropyl, n-butyl, isobutyl, tert-butyl, sec-butyl, pentyl, isopentyl, neopentyl, tert-pentyl, 3,3-dimethylbutyl, 1,1-dimethylbutyl, 1-methylpentyl, n-hexyl, isohexyl, etc. $R_8$ of —COOR$_8$, the group represented by E is a lower alkylene group which may be linear or branched. The lower alkylene group includes, for example, alkylene groups of 1 to 6 carbon atoms. Specific examples of the lower alkylene group are groups such as methylene, ethylene, propylene, butylene, 2-methylpropylene, pentylene, 2,2-dimethylpropylene, 2-ethylpropylene, hexylene, etc.

In the formulas [3] and [3a], the alkyl group represented by each of $R_5$ and $R_6$ may be linear, branched or cyclic. Preferable examples of the alkyl group are lower alkyl groups, for example, alkyl groups of 1 to 6 carbon atoms. Specific examples thereof are groups such as methyl, ethyl, n-propyl, isopropyl, n-butyl, isobutyl, tert-butyl, sec-butyl, pentyl, isopentyl, neopentyl, tert-pentyl, 3,3-dimethylbutyl, 1,1-dimethylbutyl, 1-methylpentyl, n-hexyl, isohexyl, cyclopropyl, cyclopentyl, cyclohexyl, etc. The aryl group represented by each of $R_5$ and $R_6$ includes, for example, groups such as phenyl, tolyl, xylyl, naphthyl, anthryl, etc. When $R_5$ and $R_6$ form a ring together with the nitrogen atom, aliphatic heterocyclic ammonium ions can be exemplified as the ring. The ring may further contain NH or O. As the aliphatic heterocyclic ammonium ions, for example, 5- or 6-membered aliphatic heterocyclic ammonium ions are preferable. Specific examples of the aliphatic heterocyclic ammonium ions are morpholinium ion, piperidinium ion, piperazinium ion, etc. The divalent hydrocarbon group represented by $R_7$ includes, for example, alkylene groups and divalent aromatic groups. The alkylene groups may be linear or branched. Preferable examples thereof are alkylene groups of 1 to 10 carbon atoms. Specific examples thereof are groups such as methylene, ethylene, propylene, butylene, 2-methylpropylene, pentylene, 2,2-dimethylpropylene, 2-ethylpropylene, hexylene, heptylene, octylene, 2-ethylhexylene, nonylene, decylene, cyclopropylene, cyclopentylene, cyclohexylene, etc. The divalent aromatic groups include, for example, groups such as phenylene, diphenylene, o-xylene-α,α'-diyl, —$CH_2$—$C_6H_4$—, etc.

In the formulas [4] and [4a], the alkyl groups of the trialkylammonium ion represented by $Z^+$ may be the same or different and may be linear, branched or cyclic. Preferable examples of the alkyl group are lower alkyl groups, for example, alkyl groups of 1 to 6 carbon atoms. Specific examples of the alkyl groups are groups such as methyl, ethyl, n-propyl, isopropyl, n-butyl, isobutyl, tert-butyl, sec-butyl, pentyl, isopentyl, neopentyl, tert-pentyl, 3,3-dimethylbutyl, 1,1-dimethylbutyl, 1-methylpentyl, n-hexyl, isohexyl, cyclopropyl, cyclopentyl, cyclohexyl, etc. The cyclic ammonium ion represented by $Z^+$ includes aliphatic heterocyclic ammonium ions such as morpholinium ion, piperidinium ion, piperazinium ion, etc., and aromatic heterocyclic ammonium ions such as pyridinium ion, quinolinium ion, indolinium ion, imidazolium ion, etc. These ions may have one or more substituents. The anion represented by $W^-$ includes, for example, halogen ions such as fluoride ions ($F^-$), chloride ions ($Cl^-$), bromide ions ($Br^-$), iodide ions ($I^-$), etc.; inorganic acid ions such as nitric acid ion, sulfuric acid ion, etc.; and organic acid ions such as dialkylsulfuric acid ions (e.g. dimethylsulfuric acid ion, diethylsulfuric acid ion, etc.), alkylsulfonic acid ions (e.g. methylsulfonic acid ion, ethylsulfonic acid ion, etc.), arylsulfonic acid ions (e.g. benzenesulfonic acid ion, 4-methylbenzenesulfonic acid ion, etc.), alkylcarboxylic acid ions (e.g. acetic acid ion, propionic acid ion, butyric acid ion, etc.), and arylcarboxylic acid ions (e.g. benzoic acid ion, phenylacetic acid ion, phenylpropionic acid ion, etc.).

In the formulas [5] and [5a], the alkyl groups of the dialkylamino group represented by $Z_1$ may be the same or different and may be linear, branched or cyclic. Preferable examples of the alkyl groups are lower alkyl groups, for example, alkyl groups of 1 to 6 carbon atoms. Specific examples of the alkyl groups are groups such as methyl, ethyl, n-propyl, isopropyl, n-butyl, isobutyl, tert-butyl, sec-butyl, pentyl, isopentyl, neopentyl, tert-pentyl, 3,3-dimethylbutyl, 1,1-dimethylbutyl, 1-methylpentyl, n-hexyl, isohexyl, cyclopropyl, cyclopentyl, cyclohexyl, etc. The cyclic amino group represented by $Z_1$ includes aliphatic heterocyclic amino groups and aromatic heterocyclic amino groups. As the aliphatic heterocyclic amino groups, 5- or 6-membered aliphatic heterocyclic amino groups, for example, are preferable. The aliphatic heterocyclic amino group may contain 1 to 3 heteroatoms (e.g. oxygen atom, sulfur atom, etc.) in addition to 1 to 3 nitrogen atoms. Specific examples of aliphatic heterocyclic amino group are morpholino group, piperidino group, piperazino group, etc. As the aromatic heterocyclic amino groups, 5- or 6-membered aromatic heterocyclic amino groups, for example, are preferable. The aromatic heterocyclic amino group may contain 1 to 3 heteroatoms (e.g. oxygen atom, sulfur atom, etc.) in addition to 1 to 3 nitrogen atoms. Specific examples of aromatic heterocyclic amino group are pyridyl group, quinolyl group, indolyl group, imidazolyl group, etc. These groups may have one or more substituents.

Specific examples of the amphoteric monomer of the formula [3] used in the present invention are fatty acid salts of α,β-ethylenically unsaturated carboxylic acid ester ammoniums, such as ethyl methacrylate dimethylammonium acetate N,N-dimethyl-N-methacryloyloxyethylammonioacetate, ethyl acrylate dimethylammonium, acetate N,N-dimethyl-N-acryloyloxyethylammonioacetate, ethyl methacrylate dimethylammonium propionate N,N-dimethyl-N-methacryloyloxyethylammoniopropionate, ethyl acrylate dimethylammonium propionate N,N-dimethyl-N-acryloyloxyethylammoniopropionate, methyl acrylate dimethylammonium acetate N,N-dimethyl-N-acryloloxymethylammonioacetate, propyl methacrylate dimethylammonium propionate N,N-dimethyl-N-methacryloyloxypropylammoniopropionate, butyl methacrylate dimethylammonium acetate N,N-dimethyl-N-methacryloyloxybutylammonioacetate, etc.; and vinyl heterocyclic ammonium salts such as vinylpiperidinium acetate vinylpiperidioammonioacetate, etc. The amphoteric monomer is not limited to these compounds. These compounds may be used singly or as a mixture thereof.

Specific examples of the cationic monomer of the formula [4] used in the present invention are α,β-ethylenically unsaturated carboxylic acid ester ammonium salts such as ethyl methacrylate trimethylammonium chloride, ethyl methacrylate dimethylethylammonium sulfate, propyl methacrylate dimethylethylammonium nitrate, butyl methacrylate trimethylammonium chloride, ethyl acrylate trimethylammonium sulfate, ethyl acrylate dimethylethylammonium bromide, methyl acrylate trimethylammonium nitrate, etc.; aromatic heterocyclic ammonium salts such as N-methylvinylpyridinium chloride, N-butylvinylpyridinium chloride, etc.; and aliphatic heterocyclic ammonium salts such as vinylpiperidinium chloride, etc. The cationic monomer is not limited to these compounds. These compounds may be used singly or as a mixture thereof.

Specific examples of the precursor monomer of the formula [5] are α,β-ethylenically unsaturated carboxylic acid alkylamino esters such as dimethylaminoethyl methacrylate, ethylmethylaminoethyl methacrylate, dimethylaminopropyl methacrylate, dimethylaminobutyl methacrylate, dimethylaminoethyl acrylate, ethylmethylaminoethyl acrylate, dimethylaminomethyl acrylate, etc.; α,β-ethylenically aromatic heterocyclic amines such as vinylpyridine, N-vinylcarbazole, etc.; and α,β-ethylenically aliphatic heterocyclic amines such as vinylpiperidine, etc. The precursor monomer is not limited to these compounds. These compounds may be used singly or as a mixture thereof.

In the formulas [6] and [6a], the halogen atom represented by each of $R_9$, $R_{10}$, $R_{11}$ and $R_{13}$ includes fluorine, chlorine, bromine, iodine, etc. The lower alkyl group represented by each of $R_9$, $R_{10}$ and $R_{11}$ may be linear or branched and includes, for example, alkyl groups of 1 to 6 carbon atoms. Specific examples of the lower alkyl group are groups such as methyl, ethyl, n-propyl, isopropyl, n-butyl, isobutyl, tert-butyl, sec-butyl, pentyl, isopentyl, neopentyl, tert-pentyl, 3,3-dimethylbutyl, 1,1-dimethylbutyl, 1-methylpentyl, n-hexyl, isohexyl, etc. The alkyloxycarbonyl group represented by each of $R_{10}$, $R_{11}$ and $R_{13}$ may be linear or branched and may have a double bond. It includes, for example, alkyloxycarbonyl groups of 2 to 20 carbon atoms. Specific examples of the alkyloxycarbonyl group are groups such as methyloxycarbonyl, ethyloxycarbonyl, propyloxycarbonyl, butyloxycarbonyl, pentyloxycarbonyl, hexyloxycarbonyl, heptyloxycarbonyl, octyloxycarbonyl, nonyloxycarbonyl, decyloxycarbonyl, dodecyloxycarbonyl, octadecyloxycarbonyl, ethenyloxycarbonyl, propenyloxycarbonyl, butenyloxycarbonyl, tert-butyloxycarbonyl, 2-ethylhexyloxycarbonyl, etc. The alkyl group represented by $R_{13}$ may be linear or branched and may have a double bond. It includes, for example, alkyl groups of 1 to 20 carbon atoms. Specific examples of the alkyl group are groups such as methyl, ethyl, n-propyl, isopropyl, n-butyl, isobutyl, tert-butyl, sec-butyl, pentyl, isopentyl, neopentyl, tert-pentyl, 3,3-dimethylbutyl, 1,1-dimethylbutyl, 1-methylpentyl, n-hexyl, isohexyl, heptyl, octyl, nonyl, decyl, undecyl, dodecyl, hexa-decyl, octadecyl, cyclopropyl, cyclopentyl, cyclohexyl, ethenyl, propenyl, butenyl, pentenyl, hexenyl, heptenyl, octenyl, etc. As the haloalkyl group represented by $R_{13}$, there can be exemplified haloalkyl groups of 1 to 20 carbon atoms formed by halogenation (e.g. fluorination, chlorination, bromination or iodination) of the above-exemplified alkyl groups. Specific examples of the haloalkyl group are groups such as chloromethyl, bromomethyl, trifluoromethyl, 2-chloroethyl, 3-chloropropyl, 3-bromopropyl, 3,3,3-trifluoropropyl, 2-perfluorooctylethyl, perfluorooctyl, 1-chlorodecyl, 1-chlorooctadecyl, etc. The aryl group represented by $R_{13}$ includes, for example, groups such as phenyl, tolyl, xylyl, naphthyl, anthryl, 4-methylphenyl, 4-ethylphenyl, 4-methoxyphenyl, 4-vinylphenyl, 4-chlorophenyl, etc. As the aliphatic heterocyclic group represented by $R_{13}$, 5- or 6-membered aliphatic heterocyclic groups, for example, are preferable, and there can be exemplified aliphatic heterocyclic groups containing 1 to 3 heteroatoms (e.g. nitrogen atom, oxygen atom, sulfur atom, etc.). Specific examples of the aliphatic heterocyclic group are pyrrolidyl-2-one group, piperidino group, morpholino group, etc. As the aromatic heterocyclic group represented by $R_{13}$, 5- or 6-membered aromatic heterocyclic groups, for example, are preferable, and there can be exemplified aromatic heterocyclic groups containing 1 to 3 heteroatoms (e.g. nitrogen atom, oxygen atom, sulfur atom, etc.). Specific examples of the aromatic heterocyclic group are pyridyl group, imidazolyl group, thiazolyl group, furanyl group, pyranyl group, etc. As the aralkyloxycarbonyl group represented by $R_{13}$, there can be exemplified aralkyloxycarbonyl groups of 8 to 20 carbon atoms. Specific examples of the aralkyloxycarbonyl group are benzyloxycarbonyl group, phenethyloxycarbonyl group, etc. As the acyloxy group represented by $R_{13}$, acyloxy groups of 2 to 21 carbon atoms derived from carboxylic acids are preferable. Specific examples of the acyloxy group are groups such as acetyloxy, propionyloxy, butyryloxy, pentanoyloxy, hexanoyloxy, heptanoyloxy, octanoyloxy, nonanoyloxy, decanoyloxy, benzoyloxy, etc. As the hydroxyalkyloxycarbonyl group represented by $R_{13}$, there can be exemplified hydroxyalkyloxycarbonyl groups of 2 to 20 carbon atoms formed by the replacement of the hydrogen atom of the above-exemplified alkyloxycarbonyl group by a hydroxyl group. Specific examples of the hydroxyalkyloxycarbonyl group are groups such as hydroxymethyloxycarbonyl, hydroxyethyloxycarbonyl, hydroxypropyloxycarbonyl, hydroxybutyloxycarbonyl, hydroxypentyloxycarbonyl, hydroxyhexyloxycarbonyl, hydroxyheptyloxycarbonyl, hydroxyoctyloxycarbonyl, hydroxynonyloxycarbonyl, hydroxydecyloxycarbonyl, hydroxydodecyloxycarbonyl, hydroxyoctadecyloxycarbonyl, etc. The alkylene group represented by $R_{12}$, i.e., the alkylene group which may have one or more double bonds may be linear or branched and includes, for example, alkylene groups of 1 to 10 carbon atoms. When the alkylene group has one or more double bonds, it includes alkylene groups of 1 to 10 carbon atoms having one or more, preferably 1 to 5, more preferably 1 to 3 double bonds at arbitrary positions at the ends or in the chain. Specific examples of the alkylene group are groups such as methylene, ethylene, propylene, butylene, 2-methylpropylene, pentylene, 2,2-dimethylpropylene, 2-ethylpropylene, hexylene, heptylene, octylene, 2-ethylhexylene, nonylene, decylene, ethenylene, propenylene, butenylene, pentenylene, hexenylene, butadienylene, etc. The alkylene group is not limited to these groups.

The nonionic monomer of the formula [6] includes, for example, a-olefinic aromatic hydrocarbons having 8 to 20 carbon atoms, such as styrene, 4-methylstyrene, 4-ethylstyrene, 4-methoxystyrene, divinylbenzene, etc.; ethylenically aliphatic hydrocarbons having 2 to 20 carbon atoms, such as ethylene, propylene, butylene, isobutylene, etc.; vinyl esters having 3 to 20 carbon atoms, such as vinyl formate, vinyl acetate, vinyl propionate, isopropenyl acetate, etc.; halogen-containing vinyl compounds having 2 to 20 carbon atoms, such as vinyl chloride, vinylidene chloride, vinylidene fluoride, tetrafluoroethylene, tetrachloroethylene, 4-chlorostyrene, etc.; olefin carboxylic acid esters having 4 to 20 carbon atoms, such as methyl methacrylate, ethyl methacrylate, propyl methacrylate, butyl methacrylate, 2-ethylhexyl methacrylate, lauryl methacrylate, stearyl methacrylate, vinyl methacrylate, allyl methacrylate, methyl acrylate, ethyl acrylate, butyl acrylate, 2-ethylhexyl acrylate, lauryl acrylate, stearyl acrylate, vinyl acrylate, dimethyl itaconate, diethyl itaconate, dimethyl maleate, diethyl maleate, dimethyl fumarate, diethyl fumarate, methyl crotonate, ethyl crotonate, vinyl crotonate, dimethyl citraconate, diethyl citraconate, dimethyl mesaconate, diethyl mesaconate, methyl 3-butenoate, 2-hydroxyethyl methacrylate, 3-hydroxypropyl methacrylate, 2-hydroxypropyl methacrylate, 2-hydroxyethyl acrylate, 3-hydroxypropyl acrylate, 2-hydroxypropyl acrylate, etc.; cyano-containing vinyl compounds having 3 to 20 carbon atoms, such as acrylonitrile, methacrylonitrile, allyl cyanide, etc.; olefin aldehydes having 3 to 20 carbon atoms, such as acrolein, crotonaldehyde, etc.; aliphatic heterocyclic vinyl amines having 5 to 20 carbon atoms, such as N-vinylpyrrolidone, vinylpiperidine, etc.; olefin alcohols having 3 to 20 carbon atoms, such as allyl alcohol, crotyl alcohol, etc.; and diene type compounds having 4 to 20 carbon atoms, such as butadiene, isoprene, etc. These compounds may be used singly or in proper combination. Although the molecular weight of the block copolymer of the present invention is not particularly limited, its number-average molecular weight is usually 3,000 or more, preferably 5,000 to 2,000,000, more preferably 10,000 to 1,500, 000.

As the azo group-containing polysiloxane compound used for producing the block copolymer of the present invention, any compound may be used so long as it comprises repeating units of the formula [1] or a combination of repeating units of the formula [1] and repeating units of the formula [2] and has one or more azo groups in the molecule. As to the average molecular weight of the azo group-containing polysiloxane compound, its number-average molecular weight is properly chosen in the range of usually 1,500 to 200,000, preferably 3,000 to 150,000. When the average molecular weight is low, a large amount of molecules containing no azo group are produced, so that the efficiency of production of the block copolymer is decreased, namely, the compound does not perform its essential function. When the average molecular weight is high, the compound has the following defects: its production requires a long time, and moreover since the solubility of the compound is decreased and the viscosity of a solution of the compound is increased, block copolymerization should be carried out at a low concentration of the compound, so that the rate of copolymerization with the amphoteric monomer and/or the cationic monomer, the precursor monomer, and the nonionic monomer is decreased.

In the block copolymer of the present invention comprising (a) siloxane segments and (b) amphoteric monomer units as constituent units (hereinafter abbreviated as "the amphoteric block copolymer of the present invention"), the constituting ratio of the siloxane segments (a) is not particularly limited, though it is properly chosen in the range of usually 1 to 99% by weight, preferably 5 to 95% by weight, more preferably 10 to 90% by weight.

Although the constituting ratio of the amphoteric monomer units- (b) is not particularly limited, it is properly chosen in the range of usually 1 to 99% by weight, preferably 5 to 95% by weight, more preferably 10 to 90% by weight.

When the block copolymer further comprises (d) nonionic monomer units as constituent units, the constituting ratio of the siloxane segments (a) is usually 1 to 98% by weight, preferably 5 to 90% by weight, more preferably 10 to 80% by weight. The constituting ratio of the amphoteric monomer units (b) is usually 1 to 98% by weight, preferably 5 to 90% by weight, more preferably 5 to 75% by weight. Although the constituting ratio of the nonionic monomer units (d) is also not particularly limited, it is properly chosen in the range of usually 1 to 98% by weight, preferably 5 to 90% by weight, more preferably 15 to 85% by weight.

When polymerization is carried out using a precursor monomer in the production of the amphoteric block copolymer of the present invention, the resulting block copolymer contains precursor monomer units (c) as constituent units in some cases. The above-mentioned constituting ratio of the amphoteric monomer units (b) includes the constituting ratio of precursor monomer units (c).

The percentage of precursor monomer units made amphoteric in the amphoteric block copolymer of the present invention is not particularly limited. Depending on application purpose of the block copolymer, it is preferable in some cases that the block copolymer contains precursor monomer units in part. The percentage is properly chosen in the range of usually 1 to 100%, preferably 10 to 100%.

In the block copolymer of the present invention comprising (a) siloxane segments and (b) cationic monomer units as constituent units (hereinafter abbreviated as "the cationic block copolymer of the present invention"), the constituting ratio of the siloxane segments (a) is not particularly limited, though it is properly chosen in the range of usually 1 to 99% by weight, preferably 5 to 95% by weight, more preferably 10 to 90% by weight.

Although the constituting ratio of the cationic monomer units (b) is not particularly limited, it is properly chosen in the range of usually 1 to 99% by weight, preferably 5 to 95% by weight, more preferably 10 to 90% by weight.

When the block copolymer further comprises (d) nonionic monomer units as constituent units, the constituting ratio of the siloxane segments (a) is usually 1 to 98% by weight, preferably 5 to 90% by weight, more preferably 10 to 80% by weight. The constituting ratio of the cationic monomer units (b) is usually 1 to 98% by weight, preferably 5 to 90% by weight, more preferably 5 to 75% by weight. Although the constituting ratio of the nonionic monomer units (d) is also not particularly limited, it is properly chosen in the range of usually 1 to 98% by weight, preferably 5 to 90% by weight, more preferably 15 to 85% by weight.

When polymerization is carried out using a precursor monomer in the production of the cationic block copolymer of the present invention, the resulting block copolymer contains precursor monomer units (c) as constituent units in some cases. The above-mentioned constituting ratio of the cationic monomer units (b) includes the constituting ratio of precursor monomer units (c).

The percentage of precursor monomer units converted to a quaternary salt in the cationic block copolymer of the present invention is not particularly limited. Depending on application purpose of the block copolymer, it is preferable in some cases that the block copolymer contains precursor monomer units in part. The percentage is properly chosen in the range of usually 1 to 100%, preferably 10 to 100%.

In the block copolymer of the present invention comprising (a) siloxane segments, (b) amphoteric monomer units and cationic monomer units as constituent units (hereinafter abbreviated as "the amphoteric/cationic block copolymer of the present invention"), the constituting ratio of the siloxane segments (a) is not particularly limited, though it is properly chosen in the range of usually 1 to 98% by weight, preferably 5 to 90% by weight, more preferably 10 to 80% by weight.

Although the constituting ratio of the amphoteric monomer units ($b_1$) is not particularly limited, it is properly chosen in the range of usually 1 to 98% by weight, preferably 5 to 90% by weight, more preferably 10 to 80% by weight.

Although the constituting ratio of the cationic monomer units ($b_2$) is not particularly limited, it is properly chosen in the range of usually 1 to 98% by weight, preferably 5 to 90% by weight, more preferably 10 to 80% by weight.

When the block copolymer further comprises (d) nonionic monomer units as constituent units, the constituting ratio of the siloxane segments (a) is usually 1 to 97% by weight, preferably 5 to 85% by weight, more preferably 10 to 75% by weight. The constituting ratio of the amphoteric monomer units ($b_1$) is usually 1 to 97% by weight, preferably 5 to 85% by weight, more preferably 5 to 70% by weight. The constituting ratio of the cationic monomer units ($b_2$) is usually 1 to 97% by weight, preferably 5 to 85% by weight, more preferably 5 to 70% by weight. Although the constituting ratio of the nonionic monomer units (d) is also not particularly limited, it is properly chosen in the range of usually 1 to 97% by weight, preferably 5 to 85% by weight, more preferably 15 to 80% by weight.

When polymerization is carried out using a precursor monomer in the production of the amphoteric/cationic block copolymer of the present invention, the resulting block copolymer contains precursor monomer units (c) as constituent units in some cases. The above-mentioned constituting ratio of the amphoteric monomer units ($b_1$) includes the constituting ratio of the precursor monomer units (c).

The percentage of precursor monomer units made amphoteric and the percentage of precursor monomer units converted to a quaternary salt in the amphoteric/cationic block copolymer of the present invention are not particularly limited. Depending on application purpose of the block copolymer, it is preferable in some cases that the block copolymer contains precursor monomer units in part. The percentage of precursor monomer units made amphoteric is properly chosen in the range of usually 1 to 100%, preferably 10 to 100%. The percentage of precursor monomer units converted to a quaternary salt is properly chosen in the range of usually 1 to 100%, preferably 10 to 100%.

The azo group-containing polysiloxane compound comprising repeating units of the formula [1] which is used in the present invention can easily be produced according to, for example, the process described in JP-A 4-372675, etc.

In detail, said compound can be obtained, for example, by reacting a diamine or diol compound containing a polysiloxane segment and represented by the formula [7]:

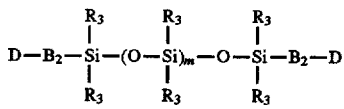

wherein D is $NH_2$ or OH; and $R_3$, $B_2$ and m are as defined above, with an azo group-containing dibasic acid dihalide of the formula [8]:

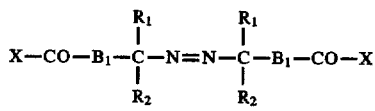

wherein X is a halogen atom; and $R_1$, $R_2$ and $B_1$ are as defined above, in a suitable solvent optionally in the presence of a basic catalyst.

As the azo group-containing polysiloxane compound comprising repeating units of the formula [1] which is used in the present invention, there may be used that produced according to, for example, the process disclosed in JP-A 6-93100, JP-A 6-322089 or the like.

In detail, said compound can be obtained also by reacting a diamine or diol compound containing a polysiloxane segment and represented by the formula [7] with an azo group-containing dibasic acid of the formula [9]:

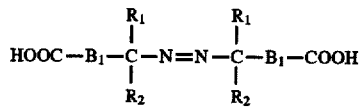

wherein $R_1$, $R_2$ and $B_1$ are as defined above, by use of a dehydrating agent in a suitable solvent optionally in the presence of a basic catalyst.

Both of the above-mentioned production processes are preferably practiced in the presence of a basic catalyst. Specific examples of the basic catalyst are organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5-4-0]undec-7-ene, tri-n-butylamine, N-methylmorpholine, etc.; metal hydrides such as sodium hydride, etc.; and basic alkali metal compounds such as n-butyllithium, etc.

Although the amount of the basic catalyst used is not particularly limited, it is properly chosen in the range of usually 0.5 to 5 moles, preferably 0.5 to 1.5 moles, per mole of the starting compound of the formula [8] or [9] or the dehydrating agent.

The dehydrating agent used in the latter process is not particularly limited so long as it can be used as a dehydrating-condensation agent. Specific examples of the dehydrating agent are inorganic dehydrating agents such as concentrated sulfuric acid, diphosphorus pentaoxide, anhydrous zinc chloride, etc.; carbodiimides such as dicyclohexylcarbodiimide, diisopropylcarbodiimide, 1-ethyl-3-(3-dimethylaminopropylcarbodiimide) hydrochloride, etc.; polyphosphoric acids; acetic anhydride; carbonyldiimidazole; and p-toluenesulfonyl chloride.

Although the amount of the dehydrating agent used is not particularly limited, it is properly chosen in the range of usually 1 to 5 moles, preferably 2 to 3 moles, per mole of the corresponding diamine or diol compound. The reason is as follows. When the amount is too small, the reaction rate is slow and only a low molecular weight can be attained. When the amount is too large, a high molecular weight can be attained in a short time, but the control of the molecular weight is difficult and the large amount is not economical.

In both processes, the solvent for reaction includes, for example, ethers such as diethyl ether, diisopropyl ether, tetrahydrofuran, dioxane, dimethoxyethane, etc.; halogenated hydrocarbons such as carbon tetrachloride, chloroform, methylene chloride, dichloroethane, trichloroethylene, etc.; hydrocarbons such as n-hexane, benzene, toluene, xylene, etc.; esters such as methyl acetate, ethyl acetate, butyl acetate, methyl propionate, etc.; acetonitrile; and N,N-dimethylformamide. These may be used singly or as a mixture thereof.

The proportions of the diamine or diol compound of the formula [7] and the azo group-containing dibasic acid dihalide of the formula [8] or the azo group-containing dibasic acid of the formula [9] are not particularly limited and are properly determined. For obtaining an azo group-containing polysiloxane having a high molecular weight, it is preferable to use the diamine or diol compound and the dihalide or the dibasic acid in substantially equimolar amounts.

Although the reaction temperature is not particularly limited, it is properly chosen in the range of usually -10° C. to 60° C. The reason is as follows. When the reaction temperature is too high, the azo groups are cleaved. When the reaction temperature is too low, the reaction rate is slow, so that the production requires a long time, and it becomes difficult to obtain an azo group-containing polysiloxane compound having a high molecular weight. The reaction temperature may be raised stepwise from a low temperature.

Although the reaction time varies depending on the production process, it is properly chosen in the range of usually 1 to 60 hours.

The desired product may be properly isolated depending on, for example, the kinds and amounts of the starting materials, basic catalyst, dihydrating agent, solvent, etc., and the condition of a reaction solution. For example, in the case of a viscous reaction solution, the reaction solution is diluted with a suitable solvent, after which impurities such as a quaternary ammonium salt produced as a by-product are removed by filtration, washing with water, etc., and then the solvent was removed, whereby the desired azo group-containing polysiloxane compound can be obtained.

For producing an azo group-containing polysiloxane compound comprising a combination of repeating units of the formula [1] and repeating units of the formula [2], the same reaction as above is carried out except for using a mixture of the azo group-containing dibasic acid dihalide of the above formula [8] and a dibasic acid dihalide of the formula X—OC—Y—CO—X (wherein X is as defined above) in place of the azo group-containing dibasic acid dihalide of the formula [8], or the same reaction as above is carried out except for using a mixture of the azo group-containing dibasic acid of the formula [9] and a dibasic acid of the formula HOOC—Y—COOH in place of the azo group-containing dibasic acid of the formula [9].

As the amphoteric monomer of the formula [3] used in the present invention, there may be used either a commercially available one or a product produced, for example, by the process disclosed in JP-A 4-95017, etc.

In detail, the amphoteric monomer of the formula [3] can easily be obtained by reacting a precursor monomer of the above formula [5] with an agent for imparting amphoteric properties, at 15°–95° C. for 30 minutes to 10 hours in a suitable solvent or without a solvent, optionally in an inert gas atmosphere such as nitrogen gas, argon gas or the like.

The agent for imparting amphoteric properties includes, for example, alkali metal salts of fatty acid halides, such as sodium monochloroacetate, potassium monochloroacetate, sodium monobromoacetate, potassium monobromoacetate, lithium monochloropropionate, sodium monoiodopropionate, sodium monoiodobutyrate, etc.; and alkali metal salts of aromatic carboxylic acid halides, such as sodium 4-chloromethylbenzoate, potassium 4-chloromethylbenzoate, etc. The agent for imparting amphoteric properties is not limited to these compounds.

The amount of the agent for imparting amphoteric properties used is properly chosen in the range of usually 0.5 to 2 moles, preferably 0.8 to 1.2 moles, per mole of the precursor monomer.

Although the concentration of the precursor monomer of the formula [5] used in making the precursor monomer amphoteric is varied depending on the kind of the monomer, it is properly chosen in the range of usually 1% by weight to 100% by weight (no solvent), preferably 20 to 80% by weight.

The solvent for reaction includes, for example, hydrocarbons such as toluene, xylene, benzene, cyclohexane, n-hexane, n-octane, etc.; halogenated hydrocarbons such as dichloroethane, trichloroethylene, etc.; esters such as methyl acetate, ethyl acetate, n-butyl acetate, methyl propionate, etc.; ketones such as acetone, methyl ethyl ketone, methyl isobutyl ketone, cyclohexanone, etc.; ethers such as diethyl ether, diisopropyl ether, tetrahydrofuran, dioxane, dimethoxyethane, etc.; alcohols such as methanol, ethanol, n-propanol, isopropanol, n-butanol, isobutanol, tert-butanol, 2-methoxyethanol, etc.; N-methylpyrrolidone; N,N-dimethylformamide; N,N-dimethylacetamide; dimethyl sulfoxide; and water. These may be used singly or as a mixture thereof.

As the cationic monomer of the formula [4] used in the present invention, there may be used either a commercially available one or a product produced, for example, by the process disclosed in JP-A 1-236211, etc.

In detail, the cationic monomer of the formula [4] can easily be obtained by reacting a precursor monomer of the above formula [5] with an agent for conversion to a quaternary salt, at 15°–90° C. for 30 minutes to 2 hours in a suitable solvent or without a solvent, optionally in an inert gas atmosphere such as nitrogen gas, argon gas or the like.

The agent for conversion to a quaternary salt includes, for example, alkyl halides such as methyl iodide, ethyl iodide, methyl bromide, ethyl bromide, methyl chloride, ethyl chloride, propyl chloride, butyl chloride, etc.; dialkylsulfuric acids such as dimethylsulfuric acid, diethylsulfuric acid, etc.; and carboxylic acid halide esters such as ethyl monochloroacetate, methyl monochloropropionate, etc. The agent for conversion to a quaternary salt is not limited to these compounds.

The amount of the agent for conversion to a quaternary salt used is properly chosen in the range of usually 0.5 to 2 moles, preferably 0.8 to 1.2 moles, per mole of the precursor monomer.

Although the concentration of the precursor monomer of the formula [5] used in its conversion to a quaternary salt is varied depending on the kind of the monomer, it is properly chosen in the range of usually 1% by weight to 100% by weight (no solvent), preferably 20 to 80% by weight. The reason is as follows. When the concentration is too high, the temperature control becomes difficult due to heat generation. When the concentration is too low, the reaction requires a long time.

The solvent for reaction includes, for example, hydrocarbons such as toluene, xylene, benzene, cyclohexane, n-hexane, n-octane, etc.; halogenated hydrocarbons such as dichloroethane, trichloroethylene, etc.; esters such as methyl acetate, ethyl acetate, n-butyl acetate, methyl propionate, etc.; ketones such as acetone, methyl ethyl ketone, methyl isobutyl ketone, cyclohexanone, etc.; ethers such as diethyl ether, diisopropyl ether, tetrahydrofuran, dioxane, dimethoxyethane, etc.; alcohols such as methanol, ethanol, n-propanol, isopropanol, n-butanol, isobutanol, tert-butanol, 2-methoxyethanol, etc.; N-methylpyrrolidone; N,N-dimethylformamide; N,N-dimethylacetamide; dimethyl sulfoxide; and water. These may be used singly or as a mixture thereof.

The block copolymers of the present invention can be produced, for example, by any of the following processes (1) to (4).

(1) A desired block copolymer of the present invention can be obtained by subjecting an azo group-containing polysiloxane compound, an amphoteric monomer and/or a cationic monomer, and optionally a nonionic monomer, to polymerization in a suitable solvent optionally in an inert gas atmosphere according to a conventional method.

(2) A desired block copolymer of the present invention can be obtained by subjecting an azo group-containing polysiloxane compound, an amphoteric monomer and/or a cationic monomer, and optionally a precursor monomer and/or a nonionic monomer, to polymerization in a suitable solvent optionally in an inert gas atmosphere according to a conventional method.

(3) An azo group-containing polysiloxane compound, a precursor monomer and optionally a nonionic monomer are subjected to polymerization in a suitable solvent optionally in an inert gas atmosphere according to a conventional method. Then, the precursor monomer units of the resulting block copolymer are made amphoteric and/or converted to a quaternary salt, whereby a desired block copolymer of the present invention can be obtained.

(4) An azo group-containing polysiloxane compound, an amphoteric monomer and/or a cationic monomer, a precursor monomer and optionally a nonionic monomer are subjected to polymerization in a suitable solvent optionally in an inert gas atmosphere according to a conventional method. Then, the precursor monomer units of the resulting block copolymer are made amphoteric and/or converted to a quaternary salt, whereby a desired block copolymer of the present invention can be obtained.

In carrying out the polymerization, the molecular weight may be controlled by adding a chain transfer agent (e.g. lauryl mercaptan, octyl metcaptan, butyl mercaptan, 2-mercaptoethanol or butyl thioglycolate) if necessary.

As a method for the above-mentioned polymerization, suspension polymerization, solution polymerization, bulk polymerization, emulsion polymerization, etc. can be exemplified. In this case, there may be used an azo group-containing polysiloxane compound and an ordinary free-radical initiator (e.g. azobisisobutyronitrile or dimethyl 2,2'-azobisisobutyrate) at the same time.

The concentrations of the azo group-containing polysiloxane compound, the amphoteric monomer, the cationic monomer, the precursor monomer and the nonionic monomer at the time of the polymerization are properly chosen so as to adjust the total concentration of these components to usually 5 to 80% by weight, preferably 10 to 60% by weight.

The polymerization is preferably carried out in the presence of an organic solvent. The organic solvent includes, for example, hydrocarbons such as toluene, xylene, benzene, cyclohexane, n-hexane, n-octane, etc.; halogenated hydrocarbons such as dichloroethane, trichloroethylene, etc.; esters such as methyl acetate, ethyl acetate, n-butyl acetate, methyl propionate, etc.; ketones such as acetone, methyl ethyl ketone, methyl isobutyl ketone, cyclohexanone, etc.; cyclic ethers such as tetrahydrofuran, dioxane, etc.; alcohols such as methanol, ethanol, n-propanol, isopropanol, n-butanol, isobutanol, tert-butanol, 2-methoxyethanol, etc.; N-methylpyrrolidone; N,N-dimethylformamide; N,N-dimethylacetamide; and dimethyl sulfoxide. These may be used singly or in proper combination. When the block copolymer of the present invention is used as a base material for cosmetic, employment of an alcohol such as ethanol or isopropanol as the solvent is preferable because the influence of the residual solvent on a human body is very slight and the block polymer can be used as a base material for cosmetic as it is after the reaction.

The polymerization is preferably carried out in an inert gas atmosphere. The inert gas includes, for example, nitrogen gas, argon gas, etc.

Although the polymerization temperature is not particularly limited, it is properly chosen in the range of usually 20°–150° C., preferably 40°–120° C. The reason is as follows. When the polymerization temperature is too low, the azo groups are not sufficiently cleaved, so that the progress of the polymerization is slow. When the polymerization temperature is too high, the azo groups are cleaved too much, so that the control of the polymerization is difficult. The reaction time varies depending on the reaction conditions such as the reaction temperature and the kinds and concentrations of the azo group-containing polysiloxane compound, the amphoteric monomer, the cationic monomer, the precursor monomer and the nonionic monomer, these monomers being properly selected for the reaction. Usually, the reaction time is properly chosen in the range of 2 to 24 hours.

It is sufficient that after-treatment after the reaction is carried out according to an after-treatment method usually employed in the art.

The block copolymer of the present invention obtained by any of the above-mentioned production processes is as follows. 1̂ When polymerization is carried out using an amphoteric monomer, or when polymerization is carried out using a precursor monomer and the precursor monomer units of the resulting block copolymer are made amphoteric, the thus obtained block copolymer is usually an amphoteric block copolymer. 2̂ When polymerization is carried out using a cationic monomer, or when polymerization is carried out using a precursor monomer and the precursor monomer units of the resulting block copolymer are converted to a quaternary salt, the thus obtained block copolymer is usually a cationic block copolymer. 3̂ When polymerization is carried out using an amphoteric monomer and a cationic monomer, or when polymerization is carried out using a precursor monomer and the precursor monomer units of the resulting block copolymer are made amphoteric and converted to a quaternary salt, or when polymerization is carried out using an amphoteric monomer or a cationic monomer and a precursor monomer and the precursor monomer units of the resulting block copolymer are converted to a quaternary salt or made amphoteric, the thus obtained block copolymer is usually an amphoteric/cationic block copolymer.

In the production of the amphoteric block copolymer of the present invention, when polymerization is carried out using a precursor monomer of the above formula [5] in place of an amphoteric monomer, the precursor monomer units of the resulting block copolymer are made amphoteric according to, for example, the production process disclosed in JP-A 4-95017, etc., whereby the amphoteric block copolymer of the present invention can easily be produced.

In detail, after the polymerization, the resulting block copolymer and the above-exemplified agent for imparting amphoteric properties in an amount of usually 0.5 to 2 moles, preferably 0.8 to 1.2 moles, per mole of the precursor monomer are reacted with each other at 15°–90° C. for 30 minutes to 10 hours in the above-exemplified suitable solvent or without a solvent, optionally in the above-exemplified inert gas atmosphere, whereby the amphoteric block copolymer of the present invention can easily be obtained. In this case, all of the precursor monomer units need not be made amphoteric and some of them may remain as they are.

When precursor monomer units remain as the constituent units of the amphoteric block copolymer of the present invention, the block copolymer having different amphoteric monomer units can be obtained by further carrying out the above-mentioned reaction using another agent for imparting different amphoteric properties.

In the production of the cationic block copolymer of the present invention, when polymerization is carried out using a precursor monomer of the above formula [5] in place of a cationic monomer, the precursor monomer units of the resulting block copolymer are converted to a quaternary salt according to, for example, the process disclosed in JP-A 7-2964, etc., whereby the cationic block copolymer of the present invention can easily be produced.

In detail, after the polymerization, the resulting block copolymer and the above-exemplified agent for conversion to a quaternary salt in an amount of usually 0.5 to 2 moles, preferably 0.8 to 1.2 moles, per mole of the precursor monomer are reacted with each other at 15°–90° C. for 30 minutes to 10 hours, optionally in the above-exemplified inert gas atmosphere, whereby the cationic block copolymer of the present invention can easily be obtained. In this case, all of the precursor monomer units need not be made amphoteric and some of them may remain as they are.

When precursor monomer units remain as the constituent units of the cationic block copolymer of the present invention, the block copolymer having different cationic monomer units can be obtained by further carrying out the above-mentioned reaction using another agent for conversion to a quaternary salt having different properties.

In the production of the amphoteric/cationic block copolymer of the present invention, when polymerization is carried out using a combination of an amphoteric monomer and a precursor monomer, a combination of a cationic monomer and a precursor monomer, or a precursor monomer, the the resulting block copolymer is subjected to the above-mentioned reaction for imparting amphoteric properties and/or the above-mentioned reaction for conversion to a quaternary salt according to, for example, the production process disclosed in JP-A 4-95017 and the like, or JP-A 7-2964 and the like, respectively, whereby the amphoteric/cationic block copolymer of the present invention can easily be produced. In this case, all of the precursor monomer units need not be made amphoteric and/or converted to a quaternary salt and some of them may remain as they are.

When precursor monomer units remain as the constituent units of the amphoteric/cationic block copolymer of the present invention, the block copolymer having different amphoteric monomer units and/or different cationic monomer units can be obtained by further carrying out the above-mentioned reaction using another agent for imparting different amphoteric properties and/or the above-mentioned reaction using another agent for conversion to a quaternary salt having different properties.

Thus obtained block copolymer of the present invention has a complicated structure and hence is difficult to represent unequivocally. When an attempt is made to represent the block copolymer by a structural formula, it can be assumed that the block polymer has any of the following structures of the formulas [10] to [12] or a combination of two or three of them.

[U-{(V)a-(G)g-(J)f-(T)b}]c    [10]

[U-{(V)a-(G)g-(J)f-(T)b}]c-U    [11]

{(V)a-(G)g-(J)f-(T)e}-[U-{(V)a-(G)g-(J)f-(T)b}]c    [12]

wherein U is a siloxane segment; V is an amphoteric monomer unit; G is a cationic monomer unit; J is a precursor monomer unit; T is a nonionic monomer unit; c is a natural number; a, b, e, f and g are independently zero or a natural number (g is a natural number in the case of a being zero, and a is a natural number in the case of g being zero); the structures in the braces { } are random structures containing various structures such as copolymers of graft type, block type, etc.

The thus obtained block copolymers of the present invention can be expected to be widely usable, for example, in resin compositions such as paint resin compositions, coating resin compositions, etc., and as base materials for cosmetics such as base materials for hair cosmetics (e.g. hair setting agent, hair treatment agent, etc.), base materials for foundational cosmetics, etc., mold release agents, coating agents, surface modifiers, medical materials, and the like.

When the block copolymer of the present invention is used for the above-exemplified purpose, it may be used after it is isolated after its synthesis and mixed with a solvent. When the block copolymer is obtained by polymerization using a solvent in which the block copolymer is soluble, the block copolymer may be used for the various purposes as it is without isolation.

When the content of amphoteric monomer units and/or cationic monomer units in the block copolymer of the present invention is high, or when a nonionic monomer used for producing the block polymer is a water-soluble compound, the block copolymer is water-soluble and hence can be effectively used, for example, in water-soluble coating materials. When the content of amphoteric monomer units and/or cationic monomer units in the block copolymer of the present invention is low, or when a nonionic monomer used for producing the block polymer is an oil-soluble compound, the block copolymer is highly water-repellent and hence can be effectively used, for example, in oil-soluble coating materials.

As a solvent used when the block copolymer of the present invention is used, for example, in a paint or coating resin composition, there can be exemplified aromatic hydrocarbons such as benzene, toluene, xylene, etc.; ketones such as acetone, methyl ethyl ketone, methyl isobutyl ketone, cyclohexanone, etc.; ethers such as diethyl ether, diisopropyl ether, tetrahydrofuran, dioxane, dimethoxyethane, etc.; lower alcohols such as methanol, ethanol, n-propanol, isopropanol, n-butanol, sec-butanol, tert-butanol, 2-methoxyethanol, etc.; and esters such as methyl acetate, ethyl acetate, butyl acetate, methyl propionate, etc. These may be used singly or in proper combination.

When the block copolymer of the present invention is used in the above-mentioned resin composition, other components may be added if necessary. As components which may be added, there can be exemplified thickeners such as alkaline earth metal oxides (e.g. magnesium oxide), alkaline earth metal hydroxides (e.g. calcium hydroxide), alkaline earth metal carbonates (e.g. calcium carbonate), etc., mold release agents such as stearic acid, etc., dyes, pigments, fillers, aggregates, defoamers, plasticizers, rust preventives, film formation assistants, ultraviolet absorbers, and the like. The components are not limited to them.

Some of the block copolymers of the present invention are highly soluble in water and ethanol. When they are used as a base material for hair cosmetic, there is possibility that they can be a base material excellent in various functions required of a base material for hair cosmetic, such as moisture resistance, setting ability, elasticity, flaking properties, feeling, etc.

When the block copolymer of the present invention is used as a base material for cosmetic after being dissolved in a hydrophilic organic solvent, the hydrophilic organic solvent includes various lower alcohols, glymes, etc. When influences on a human body are taken into consideration, more preferable examples of the hydrophilic organic solvent are ethanol, isopropanol, etc.

When the block copolymer of the present invention is used as a base material for cosmetic, other components for cosmetic may be added so long as they do not impair the function of the block copolymer. As components which may be added, there can be exemplified surfactants, fats, oils, sugars, acids, bases, buffers, salts, water, alcohols, protein derivatives, herb medicines, propellants, antiseptic and germicidal agents, antioxidants, ultraviolet absorbers, sequestering agents, oxidizing agents, reducing agents, dyes, perfumes, etc. The components are not limited to them.

When the content of amphoteric monomer units and/or cationic monomer units in the block copolymer of the present invention is high, or when a nonionic monomer used for producing the block polymer is a water-soluble compound, the block copolymer is soluble in water, alcohol or the like and hence can be expected to be usable, for example, in hairdressings of setting type, treatment type, etc., and as a base material for hair cosmetic such as a treatment agent having volume-downing effect. When the content of amphoteric monomer units and/or cationic monomer units in the block copolymer of the present invention is low, or when a nonionic monomer used for producing the block polymer is an oil-soluble compound, the block copolymer can be expected to have the following effects; when the block copolymer is used as a base material for hair cosmetic, it forms a tough coating film, so that siloxane units on the film surface improves the water-repellency, surface gloss and ease of dirt removal, and moreover the introduction of amphoteric groups and/or cationic groups improves the adhesive properties to a substrate without deterioration of the weather resistance.

The present invention is explained below in further detail with reference to Examples and Reference Examples, which are not by way of limitation but by way of illustration.

REFERENCE EXAMPLE 1

Synthesis of an azo group-containing polysiloxane compound (hereinafter abbreviated as MAI)-1

In 160 ml of methylene chloride were dissolved 3.5 g of 4-dimethylaminopyridine (hereinafter abbreviated as DMAP) and 8.0 g of 4,4'-azobis(4-cyanopentanoic acid), followed by adding thereto 125 g of an amino-modified silicone KF-8012 (a silicone of the above formula [7] wherein $R_3$ is a methyl group, D is an amino group, $B_2$ is $(CH_2)_3$, and m is about 56 on the average; a trade name; Shin-Etsu Silicone Co., Ltd.) and then 13.0 g of dicyclohexylcarbodiimide (hereinafter abbreviated as DCC), and the reaction was carried out with stirring at 20°–30° C. for 4 hours. Subsequently, the reaction mixture was diluted with 160 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 103 g of the desired product. The product was confirmed to be an azo group-containing polysiloxane amide having polysiloxane segments, from $^1$H-NMR spectrum and infrared spectrum. The azo group-containing polysiloxane amide had a number-average molecular weight of 20,000 as measured by GPC analysis, and an average number of azo groups bonded of 4.3. This amide is hereinafter abbreviated as MAI-1.

REFERENCE EXAMPLE 2

Synthesis of MAI-2

In 2,500 ml of methylene chloride were dissolved 33.7 g of DMAP and 77.3 g of 4,4'-azobis(4-cyanopentanoic acid), followed by adding thereto 1,214 g of an amino-modified silicone KF-8012 (a silicone of the above formula [7] wherein $R_3$ is a methyl group, D is an amino group, $B_2$ is $(CH_2)_3$, and m is about 56 on the average; a trade name; Shin-Etsu Silicone Co., Ltd.) and then 125 g of DCC, and the reaction was carried out with stirring at 20°–30° C. for 7 hours. Subsequently, the reaction was terminated by adding water and methanol, after which the crystals precipitated were filtered off and the filtrate was poured into a large volume of methanol to precipitate the desired compound. The supernatant was removed and the residue was dried under reduced pressure at room temperature to obtain 1,070 g of the desired product. The product was confirmed to be an azo group-containing polysiloxane amide having polysiloxane segments, from $^1$H-NMR spectrum and infrared spectrum. The azo group-containing polysiloxane amide had a number-average molecular weight of 30,000 as measured by GPC analysis, and an average number of azo groups bonded of 6.5. This amide is hereinafter abbreviated as MAI-2.

REFERENCE EXAMPLE 3

Synthesis of MAI-3

In 160 ml of methylene chloride were dissolved 3.5 g of DMAP and 8.0 g of 4,4'-azobis(4-cyanopentanoic acid), followed by adding thereto 125 g of an amino-modified silicone KF-8012 (a silicone of the above formula [7] wherein $R_3$ is a methyl group, D is an amino group, $B_2$ is $(CH_2)_3$, and m is about 56 on the average; a trade name; Shin-Etsu Silicone Co., Ltd.) and then 13.0 g of DCC, and the reaction was carried out with stirring at 20°–30° C. for 8 hours. After overnight standing, the reaction mixture was diluted with 160 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 114 g of the desired product. The product was confirmed to be an azo group-containing polysiloxane amide having polysiloxane segments, from $^1$H-NMR spectrum and infrared spectrum. The azo group-containing polysiloxane amide had a number-average molecular weight of 45,000 as measured by GPC analysis, and an average number of azo groups bonded of 9.7. This amide is hereinafter abbreviated as MAI-3.

REFERENCE EXAMPLE 4

Synthesis of MAI-4

In 160 ml of methylene chloride were dissolved 3.5 g of DMAP and 8.0 g of 4,4'-azobis(4-cyanopentanoic acid), followed by adding thereto 325 g of an amino-modified silicone KF-8008 (a silicone of the above formula [7] wherein $R_3$ is a methyl group, D is an amino group, $B_2$ is $(CH_2)_3$, and m is 150 on the average; a trade name;Shin-Etsu Silicone Co., Ltd.) and then 13.0 g of DCC, and the reaction was carried out with stirring at 20°–30° C. for 5 hours. Subsequently, the reaction mixture was diluted with 160 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 275 g of the desired product. The product was confirmed to be an azo group-containing polysiloxane amide having polysiloxane segments, from $^1$H-NMR spectrum and infrared spectrum. The azo group-containing polysiloxane amide had a number-average molecular weight of 47,000 as measured by GPC analysis, and an average number of azo groups bonded of 4.0. This amide is hereinafter abbreviated as MAI-4.

REFERENCE EXAMPLE 5

Synthesis of MAI-5

In 540 ml of methylene chloride were dissolved 13.2 g of DMAP and 30.3 g of 4,4'-azobis(4-cyanopentanoic acid), followed by adding thereto 1,230 g of an amino-modified silicone KF-8008 (a silicone of the above formula [7] wherein $R_3$ is a methyl group, D is an amino group, $B_2$ is $(CH_2)_3$, and m is 150 on the average; a trade name; Shin-Etsu Silicone Co., Ltd.) and then 49.8 g of DCC, and the reaction was carried out with stirring at 20°–30° C. for 8 hours. After overnight standing, the reaction mixture was diluted with 2,400 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 1,050 g of the desired product. The product was confirmed to be an azo group-containing polysiloxane amide having polysiloxane segments, from $^1$H-NMR spectrum and infrared spectrum. The azo group-containing polysiloxane amide had a number-average molecular weight of 86,000 as measured by GPC analysis, and an average number of azo groups bonded of 7.4. This amide is hereinafter abbreviated as MAI-5.

REFERENCE EXAMPLE 6

Synthesis of MAI-6

In 160 ml of methylene chloride were dissolved 3.5 g of DMAP and 8.0 g of 4,4'-azobis(4-cyanopentanoic acid), followed by adding thereto 325 g of an amino-modified silicone KF-8008 (a silicone of the above formula [7] wherein $R_3$ is a methyl group, D is an amino group, $B_2$ is $(CH_2)_3$, and m is 150 on the average; a trade name; Shin-Etsu Silicone Co., Ltd.) and then 13.0 g of DCC, and the reaction was carried out with stirring at 20°–30° C. for 12 hours. Subsequently, the reaction mixture was diluted with 160 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 275 g of the desired product. The product was confirmed to be an azo group-containing polysiloxane amide having polysiloxane segments, from $^1$H-NMR spectrum and infrared spectrum. The azo group-containing polysiloxane amide had a number-average molecular weight of 125,000 as measured by GPC analysis, and an average number of azo groups bonded of 10.7. This amide is hereinafter abbreviated as MAI-6.

REFERENCE EXAMPLE 7

Synthesis of MAI-7

115 Grams of a desired azo group-containing polysiloxane compound was obtained by carrying out polymerization and after-treatment in the same manner as described in Reference Example 3 except for changing the reaction time to 6.5 hours. This product was confirmed to be an azo group-containing polysiloxane amide having polysiloxane segments, from $^1$H-NMR spectrum and infrared spectrum. The azo group-containing polysiloxane amide had a number-average molecular weight of 38,000 as measured by GPC analysis, and an average number of azo groups bonded of 8.2. This amide is hereinafter abbreviated as MAI-7.

REFERENCE EXAMPLE 8

Synthesis of MAI-8

In 200 ml of methylene chloride were dissolved 4.4 g of DMAP and 10.0 g of 4,4'-azobis(4-cyanopentanoic acid), followed by adding thereto 222 g of an alcohol-modified silicone BX16-004 (a silicone of the above formula [7] wherein $R_3$ is a methyl group, D is a hydroxyl group, and m is about 90 on the average; a trade name; Toray Dow Corning Co, Ltd.) and then 16.0 g of DCC, and the reaction was carried out with stirring at 20°–30° C. for 8 hours. Subsequently, the reaction mixture was diluted with 200 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 185 g of the desired product. The product was confirmed to be an azo group-containing polysiloxane ester having polysiloxane segments, from $^1$H-NMR spectrum and infrared spectrum. This ester had a number-average molecular weight of 20,000 as measured by GPC analysis, and an average number of azo groups bonded of 2.7. The ester is hereinafter abbreviated as MAI-8.

REFERENCE EXAMPLE 9

Synthesis of MAI-9

In 1,500 ml of methylene chloride were dissolved 65.4 g of DMAP and 150.0 g of 4,4'-azobis(4-cyanopentanoic acid), followed by adding thereto 437 g of an amino-modified silicone X-22-161AS (a silicone of the above formula [7] wherein $R_3$ is a methyl group, D is an amino group, $B_2$ is $(CH_2)_3$, and m is about 9 on the average; a trade name; Shin-Etsu Silicone Co., Ltd.) and then 244 g of DCC, and the reaction was carried out with stirring at 20°–30° C. for 8 hours. Subsequently, the reaction mixture was diluted with 750 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 475 g of the desired product. The product was confirmed to be an azo group-containing polysiloxane amide having polysiloxane segments, from $^1$H-NMR spectrum and infrared spectrum. This amide had a number-average molecular weight of 12,000 as measured by GPC analysis, and an average number of azo groups bonded of 10.4. The amide is hereinafter abbreviated as MAI-9.

REFERENCE EXAMPLE 10

Synthesis of MAI-10

In 160 ml of methylene chloride were dissolved 3.5 g of DMAP and 8.0 g of 4,4'-azobis(4-cyanopentanoic acid), followed by adding thereto 125 g of an amino-modified silicone KF-8012 (a silicone of the above formula [7] wherein $R_3$ is a methyl group, D is an amino group, $B_2$ is $(CH_2)_3$, and m is about 56 on the average; a trade name; Shin-Etsu Silicone Co., Ltd.) and then 13.0 g of DCC, and the reaction was carried out with stirring at 20°–30° C. for 7.5 hours. Subsequently, the reaction was terminated by adding water and methanol, after which the crystals precipitated were filtered off and the filtrate was poured into a large volume of methanol to precipitate the desired compound. The supernatant was removed and the residue was dried under reduced pressure at room temperature to obtain 110 g of the desired product. The product was confirmed to be an azo group-containing polysiloxane amide having polysiloxane segments, from $^1$H-NMR spectrum and infrared spectrum. This amide had a number-average molecular weight of 37,200 as measured by GPC analysis, and an average number of azo groups bonded of 9.5. The amide is hereinafter abbreviated as MAI-10.

REFERENCE EXAMPLE 11

Synthesis of MAI-11

In 160 ml of methylene chloride were dissolved 3.5 g of DMAP and 8.0 g of 4,4'-azobis(4-cyanopentanoic acid), followed by adding thereto 325 g of an amino-modified silicone KF-8008 (a silicone of the above formula [7] wherein $R_3$ is a methyl group, D is an amino group, $B_2$ is $(CH_2)_3$, and m is 150 on the average; a trade name; Shin-Etsu Silicone Co., Ltd.) and then 13.0 g of DCC, and the reaction was carried out with stirring at 20°–30° C. for 5 hours. Subsequently, the reaction mixture was diluted with 160 ml of methylene chloride and the reaction was terminated by adding water and methanol. The crystals precipitated were filtered off and the filtrate was poured into a large volume of methanol to precipitate the desired compound. The supernatant was removed and the residue was dried under reduced pressure at room temperature to obtain 275 g of the desired product. The product was confirmed to be an azo group-containing polysiloxane amide having polysiloxane segments, from $^1$H-NMR spectrum and infrared spectrum. This amide had a number-average molecular weight of 127,000 as measured by GPC analysis, and an average number of azo groups bonded of 11.5. The amide is hereinafter abbreviated as MAI-11.

REFERENCE EXAMPLE 12

Synthesis of an amphoteric monomer

In 195 g of ethanol were dissolved 31.47 g of monochloroacetic acid and 18.69 g of potassium hydroxide, followed by pouring thereinto a solution of 63 g of dimethylaminoethyl methacrylate (hereinafter abbreviated as DMAEMA) in 60 g of ethanol, and the reaction was carried out with stirring at 70° C. for 6 hours. After completion of the reaction, the reaction solution was cooled, and the inorganic salt precipitated was filtered off and the filtrate was concentrated under reduced pressure. The residue was washed by addition of 500 ml of n-hexane, and washing with kneading, standing and decantation were repeated three times, followed by drying under reduced pressure. To the thus obtained viscous solution was added 300 ml of ethanol to effect dissolution, and the resulting solution was poured into 1,500 ml of acetone in small portions and stirred. The inorganic salt precipitated was filtered off and the filtrate was concentrated under reduced pressure to obtain 60.3 g (yield: 84.1%) of a desired product N,N-dimethyl-N-methacryloyloxyethylammonioacetate. The obtained amphoteric monomer was soluble in water and alcohol solvents such as methanol, ethanol, isopropanol, etc.

IR (KBr) cm$^{-1}$: 1720 (—COO—), 1630 (COO$^-$).

$^1$H-NMR δ ppm (D$_2$O): 1.956 (3H, s, C—CH$_3$), 3.42 (6H, s, N—CH$_3$), 4.00 (2H, s, N—CH$_2$—COO), 4.11 (2H, t, CH$_2$—N), 4.64 (2H, m, COO—CH$_2$), 5.79 (1H, s, CH$_2$=C), 6.18 (1H, s, CH$_2$=C).

EXAMPLE 1

Synthesis of an amphoteric block copolymer 7.5 Grams of the MAI-7 obtained in Reference Example 7, 17.5 g of DMAEMA and 50 g of ethanol were mixed and then subjected to polymerization under reflux in a nitrogen stream for 6 hours. After completion of the reaction, a suspension of 14.7 g of potassium monochloroacetate in ethanol was added to the reaction mixture, and the reaction was carried out with refluxing for 6 hours. After completion of the reaction, the inorganic salt precipitated was filtered off and the filtrate was poured into n-hexane to precipitate an amphoteric block copolymer. The copolymer was collected by filtration, washed with n-hexane, and then dried to obtain 21.6 g (yield: 54.4%) of the desired amphoteric block copolymer. From the result of $^1$H-NMR (solvent for measurement: CD$_3$OD) analysis, the composition (the ratio among monomer units) of the copolymer was found to be as follows; dimethylsiloxane segments (hereinafter abbreviated as DMS): N,N-dimethyl-N-methacryloyloxyethylammonioacetate: DMAEMA= 26.9:55.4:17.7 by weight. Table 1 shows the result of investigating the solubility of the copolymer.

EXAMPLE 2

Synthesis of an amphoteric block copolymer 17.4 Grams of DMAEMA, 14.7 g of potassium monochloroacetate and 84 g of ethanol were mixed, and the reaction was carried out with refluxing in a nitrogen stream for 6 hours. After completion of the reaction, the inorganic salt precipitated was filtered off, and 7.5 g of MAI-7 was added to the filtrate and the resulting mixture was subjected to polymerization under reflux in a nitrogen stream for 6 hours. After completion of the reaction, the reaction mixture was cooled and then poured into n-hexane to precipitate an amphoteric block copolymer. The copolymer was collected by filtration, washed with n-hexane, and then dried to obtain 27.3 g (yield: 68.7%) of the desired amphoteric block copolymer. From the result of $^1$H-NMR (solvent for measurement: CD$_3$OD) analysis, the composition (the ratio among monomer units) of the copolymer was found to be as follows; DMS : N,N-dimethyl-N-methacryloyloxyethylammonioacetate: DMAEMA= 11.3:50.2:38.5 by weight. Table 1 shows the result of investigating the solubility of the copolymer.

TABLE 1

| Example | MAI used | Monomer unit content (wt %) ① | ② | ③ | Solubility[1] Water | ④ |
|---|---|---|---|---|---|---|
| 1 | MAI-7 | 26.9 | 55.4 | 17.7 | Insoluble | Good |
| 2 | MAI-7 | 11.3 | 50.2 | 38.5 | Good | Good |

①: dimethylsiloxane (DMS) unit.
②: amphoteric monomer unit
Examples 1 and 2: N,N-dimethyl-N-methacryloyl-oxyethylammonioacetate.
③: precursor monomer unit.
④: alcohol solvents such as methanol, ethanol and isopropanol
[1]Each solution was evaluated in terms of transparency.

EXAMPLE 3

Synthesis of an amphoteric block copolymer

5 Grams of the N,N-dimethyl-N-methacryloyloxyethylammonioacetate obtained in Reference Example 12, 3 g of the MAI-7 obtained in Reference Example 7, 5 g of 2-vinylpyrrolidone (hereinafter abbreviated as VP) and 33 g of ethanol were mixed and then subjected to polymerization in a nitrogen stream at 75° C. for 0.5 hour. A stirred solution of 10 g of VP and 10 g of N,N-dimethyl-N-methacryloyloxyethylammonioacetate in 66 g of ethanol was added dropwise to the reaction mixture with stirring over a period of 2 hours, and the resulting mixture was subjected to polymerization under reflux for another 2.5 hours. After completion of the reaction, the reaction mixture was cooled and then poured into n-hexane to precipitate an amphoteric block copolymer. The copolymer was collected by filtration, washed, and then dried under reduced pressure at 80° C. for 6 hours to obtain 21 g (yield:, 63.6%) of the desired amphoteric block copolymer. From the result of $^1$H-NMR analysis, the composition (the ratio among monomer units) of the copolymer was found to be as follows; DMS : VP : N,N-dimethyl-N-methacryloyloxyethylammonioacetate=7.3:33.3:59.4 by weight.

EXAMPLE 4

Synthesis of an amphoteric block copolymer

10 Grams of the N,N-dimethyl-N-methacryloyloxyethylammonioacetate obtained in Reference Example 12, 5 g of the MAI-7 obtained in Reference Example 7, 3 g of methyl methacrylate (hereinafter abbreviated as MMA) and 54 g of ethanol were mixed and then subjected to polymerization in a nitrogen stream at 75° C. for 6 hours. After completion of the reaction, the reaction mixture was cooled and then poured into n-hexane to precipitate an amphoteric block copolymer. The copolymer was collected by filtration, washed, and then dried under reduced pressure at 80° C. for 6 hours to obtain 10 g (yield: 61.1%) of the desired amphoteric block copolymer. From the result of $^1$H-NMR analysis, the composition (the ratio among monomer units) of the copolymer was found to be as follows; DMS: MMA: N,N-dimethyl-N-methacryloyloxyethylammonioacetate=16.9:18.3:64.8 by weight.

EXAMPLE 5

Synthesis of a cationic block copolymer

20 Grams of the MAI-1 obtained in Reference Example 1, 20 g of ethyl methacrylate trimethylammonium chloride (hereinafter abbreviated as METMAC) and 100 g of isopropanol were mixed and then subjected to polymerization in a nitrogen stream at 80° C. for 5 hours.

After completion of the reaction, the reaction mixture was poured into ethyl acetate to precipitate a cationic block copolymer. The copolymer was collected by filtration, washed, and then dried under reduced pressure at 80° C. for 6 hours to obtain 24.5 g (yield: 61%) of the cationic block copolymer. From the result of $^1$H-NMR analysis, the composition (the ratio between monomer units) of the copolymer was found to be as follows; DMS: METMAC=35:65 by weight. Table 2 shows the result of investigating the solubility of the copolymer.

EXAMPLES 6 AND 7

Synthesis of cationic block copolymers

Desired cationic block copolymers were obtained in amounts of 29.2 (yield: 73%) and 22 g (yield: 55%), respectively, in the same manner as described in Example 5 except for changing the polymerization time and the polymerization temperature to 60° C. and 5 hours (Example 6) or 80° C. and 7 hours (Example 7). Table 2 shows the results of investigating the contents of monomer units and solubility of the copolymers.

EXAMPLE 8

Synthesis of a cationic block copolymer

30 Grams of the MAI-7 synthesized in Reference Example 7, 70 g of DMAEMA and 200 g of ethanol were mixed and then subjected to polymerization in a nitrogen stream at 78° C. for 6 hours. After completion of the reaction, the reaction mixture was cooled, followed by adding thereto a solution of 68.7 g of diethyl sulfate (hereinafter abbreviated as DES) in 68.7 g of ethanol, and the reaction was carried out with refluxing for 6 hours. After completion of the reaction, the reaction mixture was poured into n-hexane to precipitate a cationic block copolymer. The copolymer was collected by filtration, washed, and then dried under reduced pressure at 80° C. for 6 hours to obtain 158 g (yield: 94%) of the desired cationic block copolymer. From the result of $^1$H-NMR analysis, the composition (the ratio among monomer units) of the copolymer was found to be as follows; DMS: ethyl methacrylate dimethylethylammonium monoethylsulfate (hereinafter abbreviated as METMAMES): DMAEMA=19:45:36 by weight. Table 2 shows the result of investigating the solubility of the copolymer.

EXAMPLE 9

Synthesis of a cationic block copolymer

A desired cationic block copolymer was obtained in the same manner as in Example 8 except for changing the amount of each of DES and ethanol to 58.7 g (0.85 time as much as the theoretical amount). From the result of $^1$H-NMR analysis, the composition (the ratio among monomer units) of the copolymer was found to be as follows; DMS: METMAMES: DMAEMA=16:46:38 by weight. Table 2 shows the result of investigating the solubility of the copolymer.

EXAMPLE 10

Synthesis of a cationic block copolymer 17.5 Grams of DMAEMA and 50 g of ethanol were mixed, followed by adding thereto a solution of 17.2 g of DES in 17.2 g of ethanol, and the reaction was carried out with stirring for 6 hours. To the reaction mixture was added 7.5 g of the MAI-7 synthesized in Reference Example 7, and the resulting mixture was subjected to polymerization in a nitrogen stream at 78° C. for 6 hours. After completion of the reaction, the reaction mixture was poured into n-hexane to precipitate a cationic block copolymer. The copolymer was collected by filtration, washed, and then dried under reduced pressure at 80° C. for 6 hours to obtain 20.6 g (yield: 48.8%) of the desired cationic block copolymer. From the result of $^1$H-NMR analysis, the composition (the ratio among monomer units) of the copolymer was found to be as follows; DMS: METMAMES: DMAEMA=7:57:36 by weight. Table 2 shows the result of investigating the solubility of the copolymer.

EXAMPLE 11

Synthesis of a cationic block copolymer 10.5 Grams of the MAI-7 obtained in Reference Example 7, 3.5 g of DMAEMA, 20 g of VP and 130 g of ethanol were mixed and then subjected to polymerization in a nitrogen stream at 75° C. for 1 hour. A solution of 7 g of DMAEMA and 40 g of VP in 50 g of ethanol was added dropwise to the reaction mixture at 75° C. over a period of 3 hours, and the resulting mixture was subjected to polymerization at 75° C. for another 2.5 hours. After completion of the reaction, the reaction mixture was cooled, followed by adding thereto 9 g of DES, and the reaction was carried out at 40°–45° C. for 7 hours. After completion of the reaction, the reaction mixture was poured into n-hexane to precipitate a cationic block copolymer. The copolymer was collected by filtration, washed and then dried to obtain 73.2 g (yield: 81.3%) of the desired cationic block copolymer. From the result of $^1$H-NMR analysis, the composition (the ratio among monomer units) of the copolymer was found to be as follows; DMS: VP: DMAEMA: METMAMES=9.8:58.8:2.2:29.2 by weight. Table 2 shows the result of investigating the solubility of the copolymer.

EXAMPLE 12

Synthesis of a cationic block copolymer 3.5 Grams of DMAEMA, 3.0 g of DES and 20 g of VP were mixed, and the reaction was carried out with stirring at room temperature for 1.5 hours. After completion of the reaction, 8 g of the MAI-7 obtained in Reference Example 7 and 130 g of ethanol were added to the reaction mixture, and the resulting mixture was subjected to polymerization in a nitrogen stream at 70°–75° C. for 0.5 hour. Then, a solution prepared by reacting 7 g of DMAEMA and 6.5 g of DES in 40 g of VP for 4 hours was added dropwise to the reaction mixture over a period of 3 hours, and the resulting mixture was subjected to polymerization for another 1 hour. After completion of the reaction, the reaction mixture was poured into n-hexane to precipitate a cationic block copolymer. The copolymer was collected by filtration, washed and then dried to obtain 66.8 g (yield: 75.9%) of the desired cationic block copolymer. From the result of $^1$H-NMR analysis, the composition (the ratio among monomer units) of the copolymer was found to be as follows; DMS: VP: DMAEMA: METMAMES=8.4:58.4:3.2:30.0 by weight. Table 2 shows the result of investigating the solubility of the copolymer.

EXAMPLE 13

Synthesis of a cationic block copolymer 10.5 Grams of DMAEMA, 9.5 g of DES and 20 g of VP were mixed, and the reaction was carried out with stirring at room temperature for 1.5 hours. After completion of the reaction, 10 g of the MAI-7 obtained in Reference Example 7 and 130 g of ethanol were added to the reaction mixture, and the resulting mixture was subjected to polymerization in a nitrogen stream at 70°– 75° C. for 0.5 hour. Then, a solution of 40 g of VP in 50 g of ethanol was added dropwise to the reaction mixture over a period of 6.5 hours, and the resulting mixture was subjected to polymerization for another 0.5 hour. After completion of the reaction, the reaction mixture was poured into n-hexane to precipitate a cationic block copolymer. The copolymer was collected by filtration, washed and then dried to obtain 39.5 g (yield: 49.4%) of the desired cationic block copolymer. From the result of $^1$H-NMR analysis, the composition (the ratio among monomer units) of the copolymer was found to be as follows; DMS: VP: DMAEMA: METMAMES= 7.4:54.7:1.3:36.6 by weight. Table 2 shows the result of investigating the solubility of the copolymer.

TABLE 2

| Example | MAI used | Monomer unit content (wt %) | | | | Solubility[1] | | |
|---|---|---|---|---|---|---|---|---|
| | | ① | ② | ③ | ④ | Water | ⑤ | ⑥ |
| 5 | MAI-1 | 35 | 65 | — | — | Good | Good | — |
| 6 | MAI-1 | 26 | 74 | — | — | Good | Good | — |
| 7 | MAI-1 | 39 | 61 | — | — | Good | Good | — |
| 8 | MAI-7 | 19 | 45 | — | 36 | Good | Good | — |
| 9 | MAI-7 | 16 | 46 | — | 38 | Good | Good | — |
| 10 | MAI-7 | 7 | 57 | — | 36 | Good | Good | — |
| 11 | MAI-7 | 9.8 | 29.2 | 58.8 | 2.2 | Good | Good | Good |
| 12 | MAI-7 | 8.4 | 30.0 | 58.4 | 3.2 | Good | Good | Good |
| 13 | MAI-7 | 7.4 | 36.6 | 54.7 | 1.3 | Good | Good | Good |

①: dimethylsiloxane (DMS) unit.
②: cationic monomer unit
Examples 5 to 7: ethyl methacrylate trimethylammonium chloride
Examples 8 to 13: ethyl methacrylate dimethylethylammonium monoethylsulfate.
③: nonionic monomer unit.
④: precursor monomer unit.
⑤: alcohol solvents such as methanol, ethanol and isopropanol.
⑥: ketone solvents such as acetone.
[1]Each solution was evaluated in terms of transparency.

EXAMPLE 14

Synthesis of a cationic block copolymer

15 Grams of the MAI-5 obtained in Reference Example 5, 40 g of methyl methacrylate (hereinafter abbreviated as MMA), 3 g of DMAEMA and 120 ml of toluene were mixed and then subjected to polymerization in a nitrogen stream at 80°±2° C. for 6 hours. After completion of the reaction, the reaction mixture was cooled, followed by adding thereto 2 g of DES at 40° C., and the reaction was carried out with stirring at 40° C. for 7 hours. After completion of the reaction, the reaction mixture was poured into methanol to precipitate a cationic block copolymer. The copolymer was collected by filtration and dried to obtain 32.3 g (yield: 53.8%) of the desired cationic block copolymer. From the result of $^1$H-NMR analysis, the composition (the ratio among monomer units) of the copolymer was found to be as follows; DMS: MMA: DMAEMA: METMAMES= 36.4:54.2:3.7:5.7 by weight. The cationic block copolymer had a number-average molecular weight (Mn) and a weight-average molecular weight (Mw) of 27,600 and 43,600, respectively, as measured by GPC (eluent: THF), and a degree of dispersion (Mw/Mn) of 1.58.

EXAMPLE 15

Synthesis of a cationic block copolymer

15 Grams of the MAI-5 obtained in Reference Example 5, 40 g of MMA, 10 g of DMAEMA and 130 ml of toluene were mixed and then subjected to polymerization in a nitrogen stream at 80°±2° C. for 6 hours. After completion of the reaction, the reaction mixture was cooled, followed by adding thereto 9 g of DES at 40° C., and the reaction was carried out with stirring at 35°±5° C. for 2 hours. After completion of the reaction, the reaction mixture was poured into methanol to precipitate a cationic block copolymer. The copolymer was collected by filtration and dried to obtain 32.7 g (yield: 44.2%) of the desired cationic block copolymer. From the result of $^1$H-NMR analysis, the composition (the ratio among monomer units) of the copolymer was found to be as follows; DMS: MMA: DMAEMA: METMAMES=23.4:53.0:5.8:17.8 by weight.

EXAMPLE 16

Synthesis of a cationic block copolymer

15 Grams of the MAI-5 obtained in Reference Example 5, 40 g of MMA, 15 g of DMAEMA and 130 ml of toluene were mixed and then subjected to polymerization in a nitrogen stream at 80°±2° C. for 6 hours. After completion of the reaction, the reaction mixture was cooled, followed by adding thereto 13.5 g of DES at 40° C., and the reaction was carried out with stirring at 35°±5° C. for 2 hours. After completion of the reaction, ethanol/n-hexane was added to the reaction mixture to precipitate a cationic block copolymer, which was washed with n-hexane. The washed copolymer was collected by filtration and dried to obtain 23 g (yield: 27.5%) of the desired cationic block copolymer. From the result of $^1$H-NMR analysis, the composition (the ratio among monomer units) of the copolymer was found to be as follows; DMS: MMA: DMAEMA: METMAMES= 23.7:37.5:3.8:35.0 by weight.

EXAMPLE 17

Synthesis of a cationic block copolymer

15 Grams of the MAI-5 obtained in Reference Example 5, 20 g of MMA, 20 g of DMAEMA and 130 ml of toluene were mixed and then subjected to polymerization in a nitrogen stream at 80°±2° C. for 6 hours. After completion of the reaction, the reaction mixture was cooled, followed by adding thereto 18 g of DES at 40° C., and the reaction was carried out with stirring at 35°±5° C. for 2 hours. After completion of the reaction, ethanol/n-hexane was added to the reaction mixture to precipitate a cationic block copolymer, which was washed with n-hexane. The washed copolymer was collected by filtration and dried to obtain 28.3 g (yield: 38.8%) of the desired cationic block copolymer. From the result of $^1$H-NMR analysis, the composition (the ratio among monomer units) of the copolymer was found to be as follows; DMS: MMA: DMAEMA: METMAMES=18.2:25.0:0.6:56.2 by weight.

EXAMPLE 18

Synthesis of a cationic block copolymer

15 Grams of the MAI-5 obtained in Reference Example 5, 10 g of MMA, 30 g of DMAEMA and 130 ml of toluene were mixed and then subjected to polymerization in a nitrogen stream at 80°±2° C. for 6 hours. After completion of the reaction, the reaction mixture was cooled, followed by adding thereto 28 g of DES at 40° C., and the reaction was carried out with stirring at 35°±5° C. for 2 hours. After completion of the reaction, the reaction mixture was poured into n-hexane to precipitate a cationic block copolymer. The copolymer was collected by filtration, washed and then dried to obtain 73.1 g (yield: 88.6%) of the desired cationic block copolymer.

EXAMPLE 19

Synthesis of a cationic block copolymer

10 Grams of the MAI-7 obtained in Reference Example 7, 10 g of MMA, 30 g of DMAEMA and 130 ml of toluene were mixed and then subjected to polymerization in a nitrogen stream at 80°±2° C. for 6 hours. After completion of the reaction, the reaction mixture was cooled, followed by adding thereto 28 g of DES at 40° C., and the reaction was carried out with stirring at 35°±5° C. for 2 hours. After completion of the reaction, the reaction mixture was poured into n-hexane to precipitate a cationic block copolymer. The copolymer was collected by filtration, washed and then dried to obtain 73.6 g (yield: 94.4%) of the desired cationic block copolymer. From the result of $^1$H-NMR analysis, the composition (the ratio among monomer units) of the copolymer was found to be as follows; DMS: MMA: DMAEMA: METMAMES=12.2:24.0:2.3:61.5 by weight.

EXAMPLE 20

Synthesis of a cationic block copolymer

15 Grams of the MAI-5 obtained in Reference Example 5, 40 g of MMA, 3 g of DMAEMA and 130 ml of toluene were mixed and then subjected to polymerization in a nitrogen stream at 80°±2° C. for 6 hours. After completion of the reaction, the reaction mixture was cooled, followed by adding thereto 9 g of DES at 40° C., and the reaction was carried out with stirring at 35°±5° C. for 3 hours. After completion of the reaction, the reaction mixture was poured into n-hexane to precipitate a cationic block copolymer. The copolymer was collected by filtration, washed and then dried to obtain 53.2 g (yield: 86.0%) of the desired cationic block copolymer. From the result of $^1$H-NMR analysis, the composition (the ratio among monomer units) of the copolymer was found to be as follows; DMS: MMA: DMAEMA: METMAMES=23.5:64.4:1.4:10.7 by weight.

EXAMPLE 21

Synthesis of a cationic block copolymer

10 Grams of the MAI-5 obtained in Reference Example 5, 20 g of MMA, 20 g of DMAEMA and 130 ml of toluene were mixed and then subjected to polymerization in a nitrogen stream at 80°±2° C. for 6 hours. After completion of the reaction, the reaction mixture was cooled, followed by adding thereto 9.8 g (0.5 time as much as the theoretical amount) of DES at 40° C., and the reaction was carried out with stirring at 35°±5° C. for 3 hours. After completion of the reaction, the reaction mixture was poured into n-hexane to precipitate a cationic block copolymer. The copolymer was collected by filtration, washed and then dried to obtain 47.8 g (yield: 79.1%) of the desired cationic block copolymer. From the result of $^1$H-NMR analysis, the composition (the ratio among monomer units) of the copolymer was found to be as follows; DMS: MMA: DMAEMA: METMAMES=21.0:30.0:15.3:33.7 by weight.

EXAMPLE 22

Synthesis of a cationic block copolymer

10 Grams of the MAI-5 obtained in Reference Example 5, 20 g of MMA, 20 g of DMAEMA and 130 ml of toluene were mixed and then subjected to polymerization in a nitrogen stream at 80°±2° C. for 6 hours. After completion of the reaction, the reaction mixture was cooled, followed by adding thereto 19.6 g (the theoretical amount) of DES at 40° C., and the reaction was carried out with stirring at 35°±5° C. for 3 hours. After completion of the reaction, the reaction mixture was poured into n-hexane to precipitate a cationic block copolymer. The copolymer was collected by filtration, washed and then dried to obtain 58.9 g (yield: 84.6%) of the desired cationic block copolymer. From the result of $^1$H-NMR analysis, the composition (the ratio among monomer units) of the copolymer was found to be as follows; DMS: MMA: DMAEMA: METMAMES=16.0:37.2:0:46.8 by weight.

EXAMPLE 23

Synthesis of cationic block copolymer

10 Grams of the MAI-8 obtained in Reference Example 8, 10 g of MMA, 30 g of DMAEMA and 100 ml of toluene were mixed and then subjected to polymerization in a nitrogen stream at 80°±2° C. for 6 hours. After completion of the reaction, the reaction mixture was cooled, followed by adding thereto 25 g of DES at 40° C., and the reaction was carried out with stirring at 35°±5° C. for 2 hours. After completion of the reaction, the reaction mixture was poured into n-hexane to precipitate a cationic block copolymer. The copolymer was collected by filtration, washed with n-hexane and then dried to obtain 59.4 g (yield: 79.5%) of the desired cationic block copolymer. From the result of $^1$H-NMR analysis, the composition (the ratio among monomer units) of the copolymer was found to be as follows; DMS:MMA:DMAEMA: METMAMES=11.4:13.6:8.5:66.5 by weight.

EXAMPLE 24

Synthesis of an amphoteric/cationic block copolymer 7.5 Grams of the MAI-7 obtained in Reference Example 7, 17.5 g (0.11 mol) of DMAEMA and 50 g of ethanol were mixed and then subjected to polymerization under reflux in a nitrogen stream for 6 hours. After completion of the reaction, 1.54 g of a solution of 1.54 g (0.01 mol) of DES in ethanol was added to the reaction mixture, and the reaction was carried out with refluxing for 6 hours. After completion of the reaction, a suspension of 13.4 g of potassium monochloroacetate in ethanol was added to the reaction mixture, and the reaction was carried out with refluxing for another 6 hours. After completion of the reaction, the inorganic salt precipitated was filtered off, and the filtrate was poured into n-hexane to precipitate an amphoteric/cationic block copolymer. The copolymer was collected by filtration, washed with n-hexane and then dried to obtain 23.0 g (yield: 59.9%) of a desired amphoteric/cationic block copolymer. From the result of $^1$H-NMR (CD$_3$OD) analysis, the composition (the ratio among monomer units) of the copolymer was found to be as follows; DMS: DMAEMA: METMAMES: N,N-dimethyl-N-methacryloyloxyethylammonioacetate=16.9:13.8:10.1:59.2 by weight. Table 3 shows the result of investigating the solubility of the copolymer.

TABLE 3

| Example | MAI used | Monomer unit content (wt %) | | | | Solubility[1] | |
|---|---|---|---|---|---|---|---|
| | | ① | ② | ③ | ④ | Water | ⑤ |
| 24 | MAI-7 | 16.9 | 13.8 | 10.1 | 59.2 | Good | Good |

①: dimethylsiloxane (DMS) unit.
②: precursor monomer unit.
③: cationic monomer unit
ethyl methacrylate dimethylethylammonium monoethylsulfate.
④: amphoteric monomer unit
N,N-dimethyl-N-methacryloyloxyethylammonioacetate.
⑤: alcohol solvents such as methanol, ethanol and isopropanol.
[1]Each solution was evaluated in terms of transparency.

As described above, the present invention provides novel amphoteric block copolymers, cationic block copolymers and amphoteric/cationic block copolymers, which can be expected to be effectively usable, for example, in paint resin, coating resin compositions and as base materials for hair cosmetics. Thus, the present invention contributes greatly to the art.

What is claimed is:

1. A block copolymer comprising (a) siloxane segments, and (b) amphoteric monomer units and/or cationic monomer units, wherein the siloxane segments have repeating units of the formula:

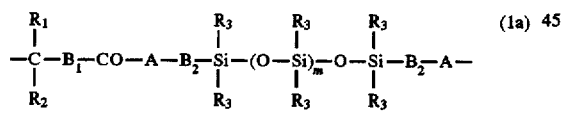

wherein $R_1$ is a hydrogen atom or a lower alkyl group; $R_2$ is a lower alkyl group or a cyano group; A is NH or O; $B_1$ is an alkylene group which can interpose one or more oxygen atoms; $R_3$ is a hydrogen atom, an alkyl group, a haloalkyl group or an aryl group; $B_2$ is a lower alkylene group which can interpose one or more oxygen atoms and/or an aromatic ring; m is zero or an integer of 1 to 200, or repeating units of a combination of the formula (1a) and the formula:

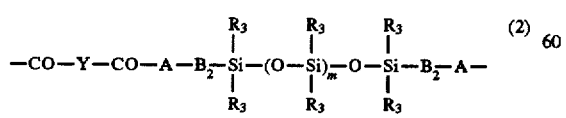

wherein —CO—Y—CO— is a dibasic acid residue; and $R_3$, A and $B_2$ and m are as defined above;

wherein the amphoteric monomer units are represented by the formula:

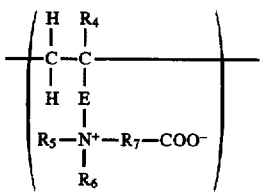

wherein $R_4$ is a hydrogen atom or a lower alkyl group; E is a direct link or —COOR$_8$—; $R_8$ is a lower alkylene group; $R_5$ and $R_6$ are independently a lower alkyl group or an aryl group, and $R_5$ or $R_6$ optionally forms a ring together with a nitrogen atom, said ring optionally containing one or more NH's or O's; $R_7$ is a divalent hydrocarbon group; and wherein the cationic monomer units are represented by the formula:

wherein $Z^+$ is a trialkylammonium ion or a cyclic ammonium ion; W is an anion; and $R_4$ and E are as defined above.

2. A block copolymer comprising (a) siloxane segments, (b) amphoteric monomer units and/or cationic monomer units, and (c) monomer units of precursors of an amphoteric or cationic monomer, wherein the siloxane segments have repeating units of the formula:

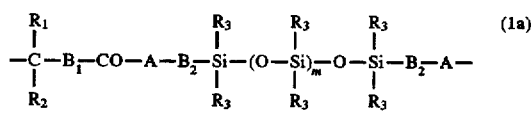

wherein $R_1$ is a hydrogen atom or a lower alkyl group; $R_2$ is a lower alkyl group or a cyano group; A is NH or O; $B_1$ is an alkylene group which can interpose one or more oxygen atoms; $R_3$ is a hydrogen atom, an alkyl group, a haloalkyl group or an aryl group; $B_2$ is a lower alkylene group which can interpose one or more oxygen atoms and/or an aromatic ring; m is zero or an integer of 1 to 200, or repeating units of a combination of the formula (1a) and the formula:

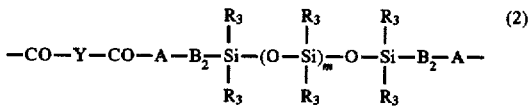

wherein —CO—Y—CO— is a dibasic acid residue; and $R_3$, A and $B_2$ and m are as defined above;

wherein the amphoteric monomer units are represented by the formula:

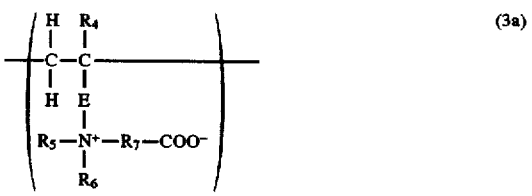

wherein $R_4$ is a hydrogen atom or a lower alkyl group; E is a direct link or —COOR$_8$—; $R_8$ is a lower alkylene group; $R_5$ and $R_6$ are independently a lower alkyl group or an aryl group, and $R_5$ or $R_6$ optionally forms a ring together with a nitrogen atom, said ring optionally containing one or more NH's or O's; $R_7$ is a divalent hydrocarbon group;

wherein the cationic monomer units are represented by the formula:

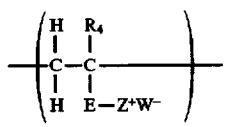
(4a)

wherein $Z^+$ is a trialkylammonium ion or a cyclic ammonium ion; $W^-$ is an anion; and $R_4$ and E are as defined above; and wherein the monomer units of precursors of an amphoteric or cationic monomer are represented by the formula:

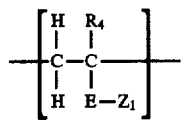
[5a]

wherein $Z_1$ is a dialkylamino group or a cyclic amino group; and $R_4$ and E are as defined above.

3. A block copolymer comprising (a) siloxane segments, (b) amphoteric monomer units and/or cationic monomer units, and (d) nonionic monomer units, wherein the siloxane segments have repeating units of the formula:

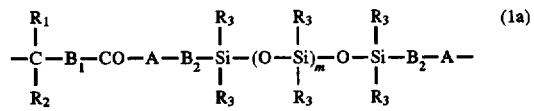
(1a)

wherein $R_1$ is a hydrogen atom or a lower alkyl group; $R_2$ is a lower alkyl group or a cyano group; A is NH or O; $B_1$ is an alkylene group which can interpose one or more oxygen atoms; $R_3$ is a hydrogen atom, an alkyl group, a haloalkyl group or an aryl group; $B_2$ is a lower alkylene group which can interpose one or more oxygen atoms and/or an aromatic ring; m is zero or an integer of 1 to 200, or repeating units of a combination of the formula (1a) and the formula:

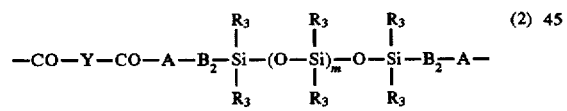
(2)

wherein —CO—Y—CO— is a dibasic acid residue; and $R_3$, A and $B_2$ and m are as defined above;

wherein the amphoteric monomer units are represented by the formula:

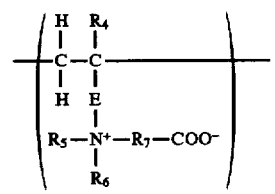
(3a)

wherein $R_4$ is a hydrogen atom or a lower alkyl group; E is a direct link or —COOR$_8$—; $R_8$ is a lower alkylene group; $R_5$ and $R_6$ are independently a lower alkyl group or an aryl group, and $R_5$ or $R_6$ optionally forms a ring together with a nitrogen atom, said ring optionally containing one or more NH's or O's; $R_7$ is a divalent hydrocarbon group;

wherein the cationic monomer units are represented by the formula:

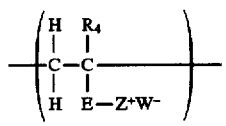
(4a)

wherein $Z^+$ is a trialkylammonium ion or a cyclic ammonium ion; $W^-$ is an anion; and $R_4$ and E are as defined above; and wherein the nonionic monomer units are represented by the formula:

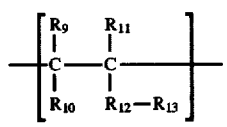
[6a]

wherein $R_9$ is a hydrogen atom, a lower alkyl group or a halogen atom; $R_{10}$ is a hydrogen atom, a lower alkyl group, a halogen atom, an alkoxycarbonyl group or a formyl group; $R_{11}$ is a hydrogen atom, a lower alkyl group, a halogen atom, or an akloxycarbonyl group; $R_{12}$ is an alkylene group which may have a double bond, or a direct link; $R_{13}$ is a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, a cyano group, an acyloxy group, a formyl group, or a hydroxyl group.

4. A block copolymer comprising (a) siloxane segments, (b) amphoteric monomer units and/or cationic monomer units, and (c) monomer units of precursors of an amphoteric or cationic monomer, and (d) nonionic monomer units, wherein the siloxane segments have repeating units of the formula:

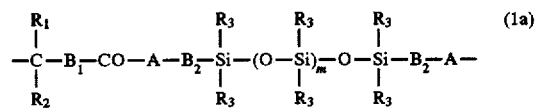
(1a)

wherein $R_1$ is a hydrogen atom or a lower alkyl group; $R_2$ is a lower alkyl group or a cyano group; A is NH or O; $B_1$ is an alkylene group which can interpose one or more oxygen atoms; $R_3$ is a hydrogen atom, an alkyl group, a haloalkyl group or an aryl group; $B_2$ is a lower alkylene group which can interpose one or more oxygen atoms and/or an aromatic ring; m is zero or an integer of 1 to 200, or repeating units of a combination of the formula (1a) and the formula:

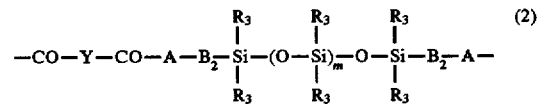
(2)

wherein —CO—Y—CO— is a dibasic acid residue; and $R_3$, A and $B_2$ and m are as defined above;

wherein the amphoteric monomer units are represented by the formula:

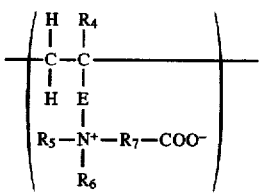

wherein R₄ is a hydrogen atom or a lower alkyl group; E is a direct link or —COOR₈—; R₈ is a lower alkylene group; R₅ and R₆ are independently a lower alkyl group or an aryl group, and R₅ or R₆ optionally forms a ring together with a nitrogen atom, said ring optionally containing one or more NH's or O's; R₇ is a divalent hydrocarbon group;

wherein the cationic monomer units are represented by the formula:

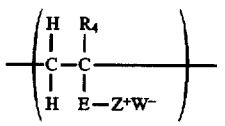

wherein $Z^+$ is a trialkylammonium ion or a cyclic ammonium ion; $W^-$ is an anion; and R₄ and E are as defined above; wherein the monomer units of precursors of an amphoteric or cationic monomer are represented by the formula:

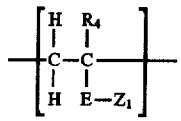

wherein $Z_1$ is a dialkylamino group or a cyclic amino group; and R₄ and E are as defined above; and wherein the nonionic monomer units are represented by the formula:

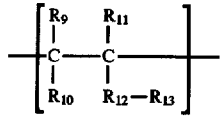

wherein R₉ is a hydrogen atom, a lower alkyl group or a halogen atom; R₁₀ is a hydrogen atom, a lower alkyl group, a halogen atom, an alkyloxycarbonyl group or a formyl group; R₁₁ is a hydrogen atom, a lower alkyl group, a halogen atom, or an alkyloxycarbonyl group; R₁₂ is an alkylene group which may have a double bond, or a direct link; R₁₃ is a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, a cyano group, an acyloxy group, a formyl group, or a hydroxyl group.

5. A process for producing the block copolymer of claim 1, which comprises polymerizing one or more amphoteric monomers and/or cationic monomers in the presence of an azo-group containing polysiloxane compound.

6. A process for producing the block copolymer of claim 3, which comprises polymerizing one or more amphoteric monomers and/or cationic monomers, and one or more nonionic monomers in the presence of an azo group-containing polysiloxane compound.

7. A process for producing the block copolymer of claim 2, which comprises polymerizing one or more amphoteric monomers and/or cationic monomers, and one more precursor monomers thereof in the presence of an azo group-containing polysiloxane compound.

8. A process for producing the block copolymer of claim 4, which comprises polymerizing one or more amphoteric monomers and/or cationic monomers, one or more Precursor monomers thereof, and one or more nonionic monomers in the presence of an azo group-containing polysiloxane compound.

9. A process for producing the block copolymer of claim 1 or 2, which comprises polymerizing one or more precursor monomers of an amphoteric or cationic monomer in the presence of an azo group-containing polysiloxane compound, followed by amphoteric ions forming reaction and/or quaternary salt forming reaction.

10. A process for producing the block copolymer of claim 3 or 4, which comprises polymerizing one or more precursor monomers of an amphoteric or cationic monomer and one or more nonionic monomers in the presence of an azo group-containing polysiloxane compound, followed by amphoteric ions forming reaction and/or quaternary salt forming reaction.

11. A process for producing the block copolymer of claim 1 or 2, which comprises polymerizing one or more amphoteric monomers and/or cationic monomers, one or more precursor monomers thereof in the presence of an azo group-containing polysiloxane compound, followed by amphoteric ions forming reaction and/or quaternary salt forming reaction.

12. A process for producing the block copolymer of claim 3 or 4, which comprises polymerizing one or more amphoteric monomers and/or cationic monomers, one or more precursor monomers thereof, and one or more nonionic monomers in the presence of an azo group-containing polysiloxane compound, followed by amphoteric ions forming reaction and/or quaternary salt forming reaction.

13. A process according to any one of claims 5 to 8, wherein the azo group-containing polysiloxane compound has repeating units of the formula:

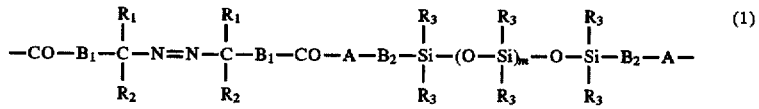

wherein R₁ is a hydrogen atom or a lower alkyl group; R₂ is a lower alkyl group or a cyano group; A is NH or O; B₁ is an alkylene group which may interpose one or more oxygen atoms; R₃ is a hydrogen atom, an alkyl group, a haloalkyl group or an aryl group; B₂ is a lower alkylene group which may interpose one or more oxygen atoms and/or an aromatic ring; and m is zero or an integer of 1 to 200, or repeating units of a combination of the formula (1) and the formula:

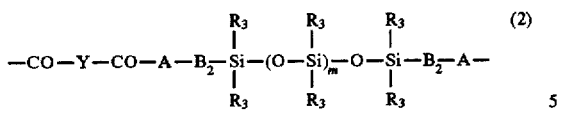

wherein —CO—Y—CO is a dibasic acid residue; and $R_3$, A, $B_2$ and m are as defined above.

14. A process according to any one of claims 5 to 8, wherein the amphoteric monomer is represented by the formula:

wherein $R_4$ is a hydrogen atom or a lower alkyl group; E is a direct linkage or —COOR$_8$—; $R_8$ is a lower alkylene group; $R_5$ and $R_6$ are independently a lower alkyl group or an aryl group, and optionally $R_5$ or $R_6$ together with a nitrogen atom forms a ring which optionally further contains one or more NH's or O's; and $R_7$ is a divalent hydrocarbon group; and the cationic monomer is represented by the formula:

wherein $Z^+$ is a trialkylammonium ion or a cyclic ammonium ion; $W^-$ is an anion; and $R_4$ and E are as defined above.

15. A process according to claim 7 or 8, wherein the precursor monomers of an amphoteric or cationic monomer are represented by the formula:

wherein $R_4$ is a hydrogen atom or a lower alkyl group; E is a direct linkage or —COOR$_8$—; $R_8$ is a lower alkylene group; and $Z_1$ is a dialkylamino group or a cyclic amino group.

16. A process according to claim 6 or 8, wherein the nonionic monomer is represented by the formula:

wherein $R_9$ is a hydrogen atom, a lower alkyl group, or a halogen atom; $R_{10}$ is a hydrogen atom, a lower alkyl group, a halogen atom, an alkyloxycarbonyl group or a formyl group; $R_{11}$ is a hydrogen atom, a lower alkyl group, a halogen atom or an alkyleneoxycarbonyl group; $R_{12}$ is an alkylene group which may contain a double bond or a direct linkage; and $R_{13}$ is a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, a cyano group, an acyloxy group, a formyl group or a hydroxyl group.

17. A block copolymer according to claim 1, wherein the amphoteric monomer units are derived from a compound of the formula:

wherein $R_4$, E, $R_5$, $R_6$ and $R_7$ are as defined in claim 22, and the cationic monomer units are derived from a compound of the formula:

wherein $R_4$, E, Z and $W^-$ are as defined in claim 22.

18. A block copolymer according to claim 17, wherein $W^-$ is a halogen ion, an inorganic acid ion, a dialkylsulfonic acid ion, an alkylsulfonic acid ion, an arylsulfonic acid ion, an alkylcarboxylic acid ion, or an arylcarboxylic acid ion.

19. A block copolymer according to claim 2, wherein the amphoteric monomer units are derived from a compound of the formula:

wherein $R_4$, E, $R_5$, $R_6$ and $R_7$ are as defined in claim 23, the cationic monomer units are derived from a compound of the formula:

wherein $R_4$, E, $Z^+$, and $W^-$ are as defined in claim 23, and the monomer units of precursors of an amphoteric or cationic monomer are derived from a compound of the formula:

wherein $Z^1$, $R_4$ and E are as defined in claim 23.

20. A block copolymer according to claim 19, wherein $W^-$ is a halogen ion, an inorganic acid ion, a dialkylsulfonic acid ion, an alkylsulfonic acid ion, an arylsulfonic acid ion, an alkylcarboxylic acid ion, or an arylcarboxylic acid ion.

21. A block copolymer according to claim 3, wherein the amphoteric monomer units are derived from a compound of the formula:

wherein $R_4$, E, $R_5$, $R_6$ and $R_7$ are as defined in claim 3, the cationic monomer units are derived from a compound of the formula:

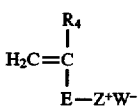 (4)

wherein $R_4$, E, $Z^+$ and $W^-$ are as defined in claim 3, and the nonionic monomer units are derived from a compound of the formula:

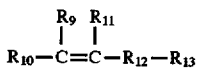 (6)

wherein $R_9$, $R_{10}$, $R_{11}$, $R_{12}$ and $R_{13}$ are as defined in claim 3.

22. A block copolymer according to claim 21, wherein $W^-$ is a halogen ion, an inorganic acid ion, a dialkylsulfonic acid ion, an alkylsulfonic acid ion, an arylsulfonic acid ion, an alkylcarboxylic acid ion, or an arylcarboxylic acid ion.

23. A block copolymer according to claim 4, wherein the amphoteric monomer units are derived from a compound of the formula:

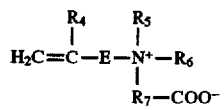 (3)

wherein $R_4$, E, $R_5$, $R_6$ and $R_7$ are as defined in claim 25, the cationic monomer units are derived from a compound of the formula:

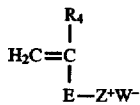 (4)

wherein $R_4$, E, $Z^+$ and $W^-$ are as defined in claim 4,
the monomer units of precursors of an amphoteric or cationic monomer are derived from a compound of the formula:

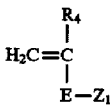 (5)

wherein $Z_1$, $R_4$ and E are as defined in claim 4, and the nonionic monomer units are derived from a compound of the formula:

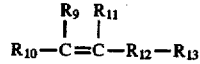 (6)

wherein $R_9$, $R_{10}$, $R_{11}$, $R_{12}$ and $R_{13}$ are as defined in claim 4.

24. A block copolymer according to claim 17, wherein the compound of the formula (3) is at least one member selected from the group consisting of ethyl methacrylate dimethylammonium acetate, ethyl acrylate dimethylammonium acetate, ethyl methacrylate dimethylammonium propionate, ethyl acrylate dimethylammonium propionate, methyl acrylate dimethylammonium acetate, propyl methacrylate dimethylammonium propionate, butyl methacrylate dimethylammonium acetate, and vinylpiperidinium acetate; and the compound of the formula (4) is at least one member selected from the group consisting of ethyl methacrylate trimethylammonium chloride, ethyl methacrylate dimethylethylammonium sulfate, propyl methacrylate dimethylethylammonium nitrate, butyl methacrylate trimethylammonium chloride, ethyl acrylate trimethylammonium sulfate, ethyl acrylate dimethylethylammonium bromide, methyl acrylate trimethylammonium nitrate, ethyl methacrylate dimethylethylammonium monoethyl sulfate, N-methylvinylpyridinium chloride, N-butylvinylpyridinium chloride, and vinylpiperidinium chloride.

25. A block copolymer according to claim 19, wherein the compound of the formula (3) is at least one member selected from the group consisting of ethyl methacrylate dimethylammonium acetate, ethyl acrylate dimethylammonium acetate, ethyl methacrylate dimethylammonium propionate, ethyl acrylate dimethylammonium propionate, methyl acrylate dimethylammonium acetate, propyl methacrylate dimethylammonium propionate, butyl methacrylate dimethylammonium acetate, and vinylpiperidinium acetate;

the compound of the formula (4) is at least one member selected from the group consisting of ethyl methacrylate trimethylammonium chloride, ethyl methacrylate dimethylethylammonium sulfate, propyl methacrylate dimethylethylammonium nitrate, butyl methacrylate trimethylammonium chloride, ethyl, acrylate trimethylammonium sulfate, ethyl acrylate dimethylethylammonium bromide, methyl acrylate trimethylammonium nitrate, ethyl methacrylate dimethylethylammonium monoethyl sulfate, N-methylvinylpyridinium chloride, N-butylvinylpyridinium chloride, and vinylpiperidinium chloride; and the compound of the formula (5) is at least one member selected from the group consisting of dimethylaminoethyl methacrylate, ethylmethylaminoethyl methacrylate, dimethylaminopropyl methacrylate, dimethylaminobutyl methacrylate, dimethylaminoethyl acrylate, ethylmethylaminoethyl acrylate, dimethylaminomethyl acrylate, vinylpyridine, N-vinylcarbazole, and vinylpiperidine.

26. A block copolymer according to claim 22, wherein the compound of the formula (3) is at least one member selected from the group consisting of ethyl methacrylate dimethylammonium acetate, ethyl acrylate dimethylammonium acetate, ethyl methacrylate dimethylammonium propionate, ethyl acrylate dimethylammonium propionate, methyl acrylate dimethylammonium acetate, propyl methacrylate dimethylammonium propionate, butyl methacrylate dimethylammonium acetate, and vinylpiperidinium acetate;

the compound of the formula (4) is at least one member selected from the group consisting of ethyl methacrylate trimethylammonium chloride, ethyl methacrylate dimethylethylammonium sulfate, propyl methacrylate dimethylethylammonium nitrate, butyl methacrylate trimethylammonium chloride, ethyl acrylate trimethylammonium sulfate, ethyl acrylate dimethylethylammonium bromide, methyl acrylate trimethylammonium nitrate, ethyl methacrylate dimethylethylammonium monoethyl sulfate, N-methylvinylpyridinium chloride, N-butylvinylpyridinium chloride, and vinylpiperidinium chloride; and the compound of the formula (6) is at least one member selected from the group consisting of styrene, 4-methylstyrene, 4-ethylstyrene, 4-methoxystyrene, divinylbenzene, ethylene, propylene, butylene, isobutylene, vinyl formate, vinyl acetate, vinyl propionate, isopropenyl acetate, vinyl chloride, vinylidene chloride, vinylidene fluoride, tetrafluoroethylene, tetrachloroethylene, 4-chlorostyrene, methyl methacrylate, ethyl methacrylate, propyl methacrylate, butyl methacrylate, 2-ethylhexyl methacrylate, lauryl methacrylate, stearyl methacrylate, vinyl methacrylate, allyl methacrylate, methyl acrylate, ethyl acrylate, butyl acrylate, 2-ethylhexyl acrylate, lauryl acrylate, stearyl acrylate, vinyl acrylate, dimethyl itaconate, diethyl itaconate, dimethyl maleate, diethyl maleate, dimethyl fumarate, diethyl fumarate, methyl crotonate, ethyl crotonate, vinyl crotonate, dimethyl citraconate, diethyl citraconate, dimethyl mesaconate, diethyl mesaconate, methyl 3-butenoate, 2-hydroxyethyl methacrylate, 3-hydroxypropyl methacrylate 2-hydroxypropyl methacrylate, 2-hydroxyethyl acrylate, 3-hydroxypropyl acrylate, 2-hydroxypropyl acrylate, acrylonitrile, methacrylonitrile, allyl cyanide, acrolein, crotonaldehyde, N-vinylpyrrolidone, vinylpiperidine, allyl alcohol, crotyl alcohol, butadiene, and isoprene.

27. A block copolymer according to claim 23, wherein the compound of the formula (3) is at least one member selected from the group consisting of ethyl methacrylate dimethylammonium acetate, ethyl acrylate dimethylammonium acetate, ethyl methacrylate dimethylammonium propionate, ethyl acrylate dimethylammonium propionate, methyl acrylate dimethylammonium acetate, propyl methacrylate dimethylammonium propionate, butyl methacrylate dimethylammonium acetate, and vinylpiperidinium acetate;

the compound of the formula (4) is at least one member selected from the group consisting of ethyl methacrylate trimethylammonium chloride, ethyl methacrylate dimethylethylammonium sulfate, propyl methacrylate dimethylethylammonium nitrate, butyl methacrylate trimethylammonium chloride, ethyl acrylate trimethylammonium sulfate, ethyl acrylate dimethylethylammonium bromide, methyl acrylate trimethylammonium nitrate, ethyl methacrylate dimethylethylammonium monoethyl sulfate, N-methylvinylpyridinium chloride, N-butylvinylpyridinium chloride, and vinylpiperidinium chloride; and the compound of the formula (5) is at least one member selected from the group consisting of dimethylaminoethyl methacrylate, ethylmethylaminoethyl methacrylate, dimethylaminopropyl methacrylate, dimethylaminobutyl methacrylate, dimethylaminoethyl methacrylate, ethylmethylaminoethyl acrylate, dimethylaminomethyl acrylate, vinylpyridine, N-vinylcarbazole, and vinylpiperidine; and the compound of the formula (6) is at least one member selected from the group consisting of styrene, 4-methylstyrene, 4-ethylstyrene, 4-methoxystyrene, divinylbenzene, ethylene, propylene, butylene, isobutylene, vinyl formate, vinyl acetate, vinyl propionate, isopropenyl acetate, vinyl chloride, vinylidene chloride, vinylidene fluoride, tetrafluoroethylene, tetrachloroethylene, 4-chlorostyrene, methyl methacrylate, ethyl methacrylate, propyl methacrylate, butyl methacrylate, 2-ethylhexyl methacrylate, lauryl methacrylate, stearyl methacrylate, vinyl methacrylate, allyl methacrylate, methyl acrylate, ethyl acrylate, butyl acrylate, 2-ethylhexyl acrylate, lauryl acrylate, stearyl acrylate, vinyl acrylate, dimethyl itaconate, diethyl itaconate, dimethyl maleate, diethyl maleate, dimethyl fumarate, diethyl fumarate, methyl crotonate, ethyl crotonate, vinyl crotonate, dimethyl citraconate, diethyl citraconate, dimethyl mesaconate, diethyl mesaconate, methyl 3-butenoate, 2-hydroxyethyl methacrylate, 3-hydroxypropyl methacrylate 2-hydroxypropyl methacrylate, 2-hydroxyethyl acrylate, 3-hydroxypropyl acrylate, 2-hydroxypropyl acrylate, acrylonitrile, methacrylonitrile, allyl cyanide, acrolein, crotonaldehyde, N-vinylpyrrolidone, vinylpiperidine, allyl alcohol, crotyl alcohol, butadiene, and isoprene.

28. A block copolymer according to claim 23, wherein $W^-$ is a halogen ion, an inorganic acid ion, a dialkylsulfonic acid ion, an alkylsulfonic acid ion, an arylsulfonic acid ion, an alkylcarboxylic acid ion, or arylcarboxylic acid ion.

* * * * *